US007274623B2

(12) United States Patent
Bayram et al.

(10) Patent No.: US 7,274,623 B2
(45) Date of Patent: Sep. 25, 2007

(54) METHOD AND SYSTEM FOR OPERATING CAPACITIVE MEMBRANE ULTRASONIC TRANSDUCERS

(75) Inventors: Baris Bayram, Stanford, CA (US); Ömer Oralkan, Mountain View, CA (US); Butrus T. Khuri-Yakub, Palo Alto, CA (US)

(73) Assignee: Board of Trustees of the Deland Stanford Junior University, Stanford, CA (US)

( * ) Notice: Subject to any disclaimer, the term of this patent is extended or adjusted under 35 U.S.C. 154(b) by 252 days.

(21) Appl. No.: 11/094,874

(22) Filed: Mar. 30, 2005

(65) Prior Publication Data

US 2005/0234342 A1 Oct. 20, 2005

Related U.S. Application Data

(60) Provisional application No. 60/615,319, filed on Sep. 30, 2004, provisional application No. 60/608,788, filed on Sep. 10, 2004, provisional application No. 60/560,333, filed on Apr. 6, 2004.

(51) Int. Cl.
*B06B 1/02* (2006.01)
*H02K 7/00* (2006.01)
*A61B 8/00* (2006.01)

(52) U.S. Cl. ...................... 367/140; 310/324; 310/334; 600/437; 600/459

(58) Field of Classification Search ................ 600/437, 600/459; 367/140; 438/53; 310/324, 334
See application file for complete search history.

(56) References Cited

U.S. PATENT DOCUMENTS

2005/0200241 A1 * 9/2005 Degertekin ................. 310/334
2005/0219953 A1 * 10/2005 Bayram et al. ............. 367/178
2006/0279174 A1 * 12/2006 Oliver et al. ............... 310/338

* cited by examiner

*Primary Examiner*—Evan Pert
(74) *Attorney, Agent, or Firm*—Perkins Coie LLP

(57) ABSTRACT

A novel operation regime for capacitive micromachined ultrasonic transducers (cMUTs). The collapse-snapback operation in which the center of the membrane makes intermittent contact with the substrate. This combines two distinct states of the membrane (in-collapse and out-of-collapse) to unleash unprecedented acoustic output pressures into the medium. The collapse-snapback operation utilizes a larger range of membrane defection profiles (both collapsed and released membrane profiles) and generates higher acoustic output pressures than the conventional operation. Collapse-snapback operation meets the extreme acoustic transmit pressure demands of the ultrasonic industry.

11 Claims, 29 Drawing Sheets

METHOD AND SYSTEM FOR OPERATING CAPACITIVE MEMBRANE ULTRASONIC TRANSDUCERS

CROSS-REFERENCES TO RELATED APPLICATIONS

This application claims priority to U.S. Provisional Patent Application No. 60/560,333 filed Apr. 6, 2004 and U.S. Provisional Patent Application No. 60/615,319 filed Sep. 30, 2004, and U.S. Provisional Patent Application No. 60/608,788 filed Sep. 10, 2004.

BRIEF DESCRIPTION OF THE INVENTION

This invention relates generally to micro-electro-mechanical systems (MEMS) and particularly to capacitive membrane ultrasonic transducers (cMUTs), and describes a novel method and system for their operation in collapse snapback of the membrane.

BACKGROUND OF THE INVENTION

Capacitive membrane ultrasonic transducers have a metal coated membrane such as silicon or silicon nitride supported above a substrate by an insulating layer such as silicon oxide, silicon nitride or other insulating material. The substrate may be a highly doped semiconductor material such as silicon or may be undoped silicon with a metal layer. The thin metal covering the membrane and the highly doped substrate or metal layer form the two electrodes of a capacitor. Generally the substrate, support and membrane form a cell which may be evacuated. Generally the transducers comprise a plurality of cells of the same or different sizes and shapes. In operation, the cells may be arranged in arrays with the electrical excitation generating beam patterns. Typically transducer cells have sizes ranging between 5 μm and 1000 μm in diameter.

The fabrication and operation of capacitive membrane transducers is described in many publications and patents. For example U.S. Pat. Nos. 5,619,476, 5,870,351 and 5,894,452, incorporated herein by reference, describe fabrication using surface machining technologies. Pending Application Ser. No. 60/683,057 filed Aug. 7, 2003, incorporated herein by reference, describes fabrication by using wafer bonding techniques. Such transducers are herein referred to a capacitive micromachined transducers (cMUTS).

The active part of a cMUT is the metal-coated membrane. A DC bias voltage applied between the membrane and the bottom electrodes creates electrostatic attraction, pulling the membrane toward the substrate. If an AC voltage is applied to a biased membrane, harmonic membrane motion is obtained. The DC bias voltage strongly affects the AC vibrational amplitude. As the DC voltage is increased, a larger sinusoidal membrane motion increases the transmitted acoustic pressure. To achieve maximum efficiency, the conventional operation of the cMUT requires a bias voltage close to the collapse voltage, the voltage at which the membrane contacts the substrate. In conventional operation the sum of the DC bias and the applied AC signal must not exceed the collapse voltage. Therefore, total acoustic output pressure is limited by the maximum allowed AC voltage.

If a biased cMUT membrane is subject to an impinging ultrasonic pressure field, the membrane motion generates AC detection currents. This current amplitude increases with increasing DC bias voltage. To maximize the receive sensitivity, the bias voltage is increased close to the collapse voltage. Again, it is required that the sum of the bias voltage and the received voltage due to the motion caused by the ultrasonic pressure field be less than the collapse voltage. In co-pending application Ser. No. 11/078,795 filed Mar. 10, 2005 there is described a method of operating the transducers with the membrane collapsed. In this regime, the membrane is first biased at a voltage higher than the collapse voltage, therefore initially collapsing the membrane onto the substrate. Then, the DC bias is changed to a level, which is larger than the snapback voltage to ensure the collapsed membrane state. At this operating DC voltage, the center of the membrane remains in contact with the substrate. By adding an AC voltage, harmonic membrane motion is obtained in a circular ring concentric to the center. In this regime, the ultrasonic transducer has a higher electromechanical coupling efficiency than it has when it is operated in the conventional pre-collapse regime.

There is nevertheless a need for a method of operating cMUTs to generate higher acoustic output pressures than either the conventional or collapsed method of operation. An ultrasonic transducer which produces high transmit pressures will meet the extreme acoustic transmit pressure demands of the ultrasonic industry.

OBJECTS AND SUMMARY OF THE INVENTION

It is a general object of the person and invention to provide a method of operation cMUTs so that they generate high acoustic output pressures.

It is a further object of the present invention to provide a method of operating cMUTs with a wide range of membrane deflection profiles.

It is a further object of the present invention to provide a method of operating a cMUT in the collapsed-snapback regime.

The invention is directed to a method of operating a cMUT transducer in a membrane collapse-snapback regime. First the membrane collapse and snapback voltages for the transducer are determined. A DC voltage greater than the collapse voltage then biases the membrane into collapse. A voltage pulse is then applied which is greater than the snapback voltage to cause the membrane to snapback. When the pulse is terminated the membrane collapses under the influence of the bias voltage. In an alternative mode the DC bias voltage is less than the snapback voltage and a voltage pulse greater than the collapse voltage is applied to cause the membrane to collapse. When the pulse is terminated the membrane snaps back. Acoustic pressure waves are generated both in snapback and collapse of the membrane alternating pulses will cause intermittent collapse and snapback to generate ultrasonic acoustic waves.

BRIEF DESCRIPTION OF THE DRAWINGS

The foregoing and other objects of the invention will be more clearly understood from reading the following description of the invention in conjunction with the accompanying drawings in which:

FIG. 9(*b*) is a diagram showing experimental results in the form of a graph of Average Membrane Pressure (MPa) versus Time (μs).

FIG. 9(*c*) is a diagram showing experimental results in the form of a graph of Average Membrane Pressure (MPa) versus Time (μs).

FIG. 9(*d*) is a diagram showing experimental results in the form of a graph of Average Membrane Pressure (MPa) versus Time (μs).

FIG. 11(*b*) is a diagram showing experimental results in the form of a graph of Peak-to-Peak Pressure Per Volt (kPaN) versus Unipolar Pulse Amplitude (V).

FIG. 11(*c*) is a diagram showing experimental results in the form of a graph of Peak-to-Peak Pressure (MPa) versus Bipolar Pulse Amplitude (V).

FIG. 11(*d*) is a diagram showing experimental results in the form of a graph of Peak-to-Peak Pressure Per Volt (kPa/V) versus Bipolar Pulse Amplitude (V).

FIG. 11(*e*) is a diagram showing experimental results in the form of a graph of Peak-to-Peak Pressure (MPa) versus Bias Voltage (V).

FIG. 11(*f*) is a diagram showing experimental results in the form of a graph of Peak-to-Peak Pressure (MPa) versus Bias Voltage (V).

DESCRIPTION OF THE PREFERRED EMBODIMENTS

Figure 1:
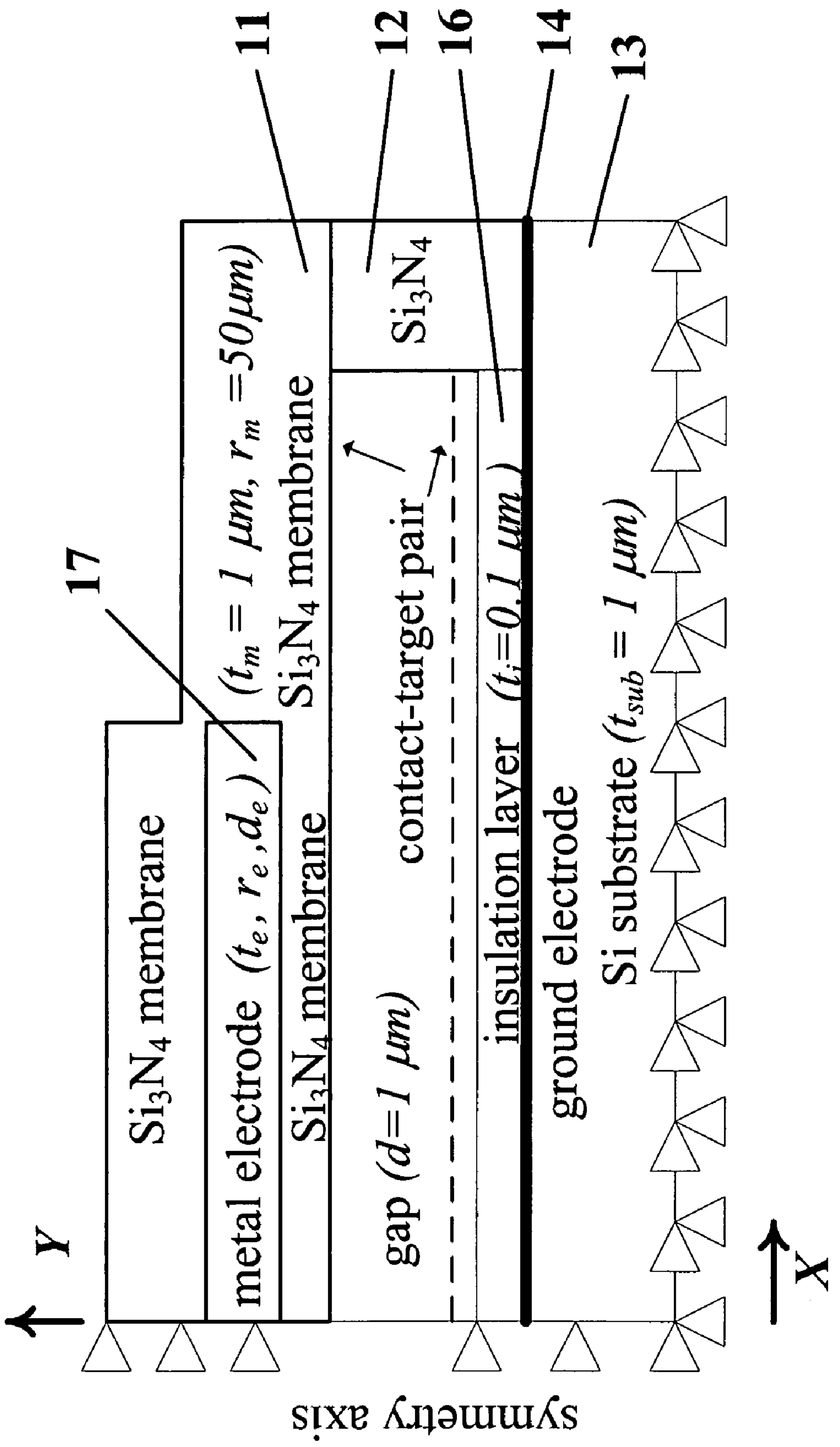
FIG. 1 schematically shows a cMUT cell.

A circular capacitive micromachined ultrasonic transducer (cMUT) is illustrated in FIG. 1. The transducer includes a silicon nitride membrane 11. A silicon nitride ring 12 supports the membrane above a silicon substrate 13. An infinitesimally thin ground electrode 14 is located on the top surface of the substrate. An insulating layer 16 is formed on the ground electrode. The gap between the membrane and the insulating layer is under vacuum. The other electrode 17, made of aluminum, is an integral part of the membrane 11. In the example to be described the electrode dimensions are defined as the radius ($r_e$) and the thickness as ($t_e$). The electrode is circular and coaxial with the membrane. The vertical distance ($d_e$) between the bottom of the membrane and the metal electrode determines the electrode position. The dimensions of the cell to be discussed are shown in FIG. 1.

The present invention is directed to a novel operation regime for capacitive micromachined ultrasonic transducers (cMUTs) of the type shown in FIG. 1. The collapse-snapback operation regime, in which the center of the membrane makes intermittent contact with the substrate. This combines two distinct states of the membrane (in-collapse and out-of-collapse) to unleash unprecedented acoustic output pressures (~10 MPa) into the medium. To achieve maximum efficiency, the conventional operation of the cMUT requires a bias voltage close to the collapse voltage. Total acoustic output pressure is limited by the efficiency of the cMUT, and by the maximum-allowed pulse voltage on the membrane. The collapse-snapback operation overcomes the above-mentioned limitations of the conventional operation. The collapse-snapback operation utilizes a larger range of membrane defection profiles (both collapsed and released membrane profiles) and generates higher acoustic output pressures than the conventional operation. Collapse-snapback operation meets the extreme acoustic transmit pressure demands of the ultrasonic industry.

Figure 2A:
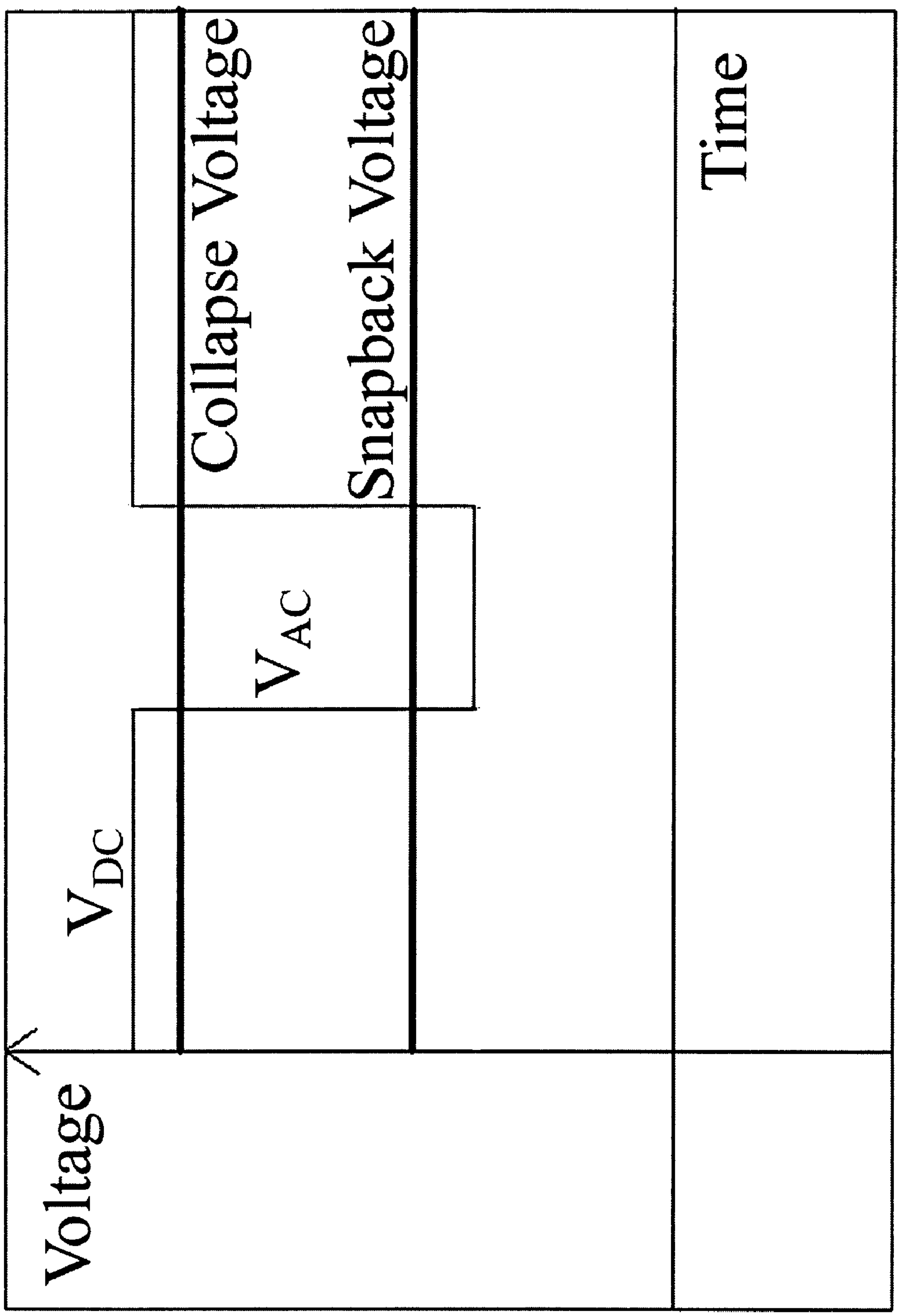
FIGS. 2*a* and 2*b* show applied voltages for operation of cMUT in accordance with the present invention.
Figure 2B:
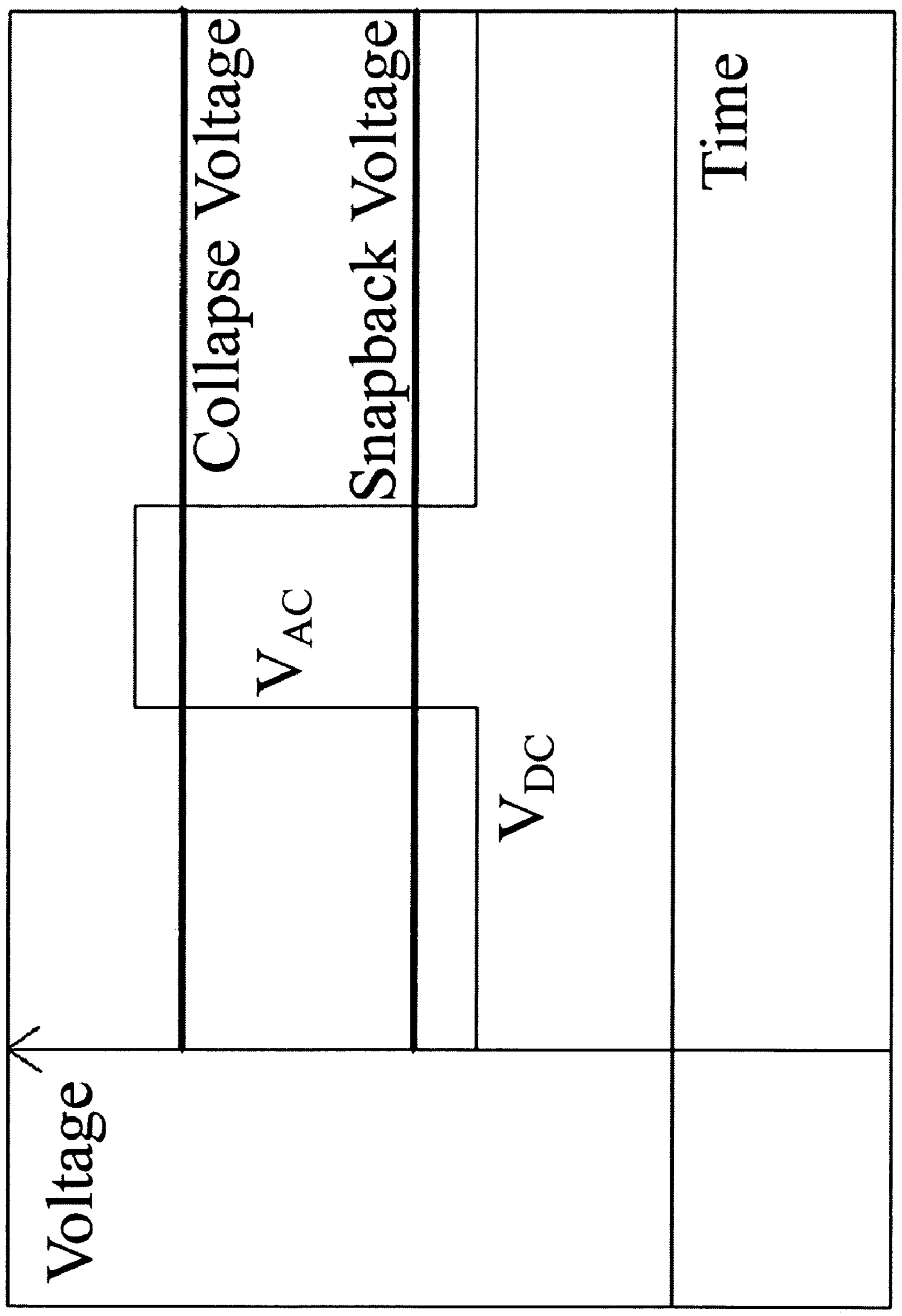

In operation the collapse and snapback voltages are determined. Then a DC bias voltage is applied to bias the transducer so that the membrane is either in its collapsed state or its snapback states. Thereafter an intermittent pulse having an amplitude which has peak values greater than the collapse voltage and minimum values below the snapback voltage are applied. This causes the membrane to oscillate between the collapse and snapback state. This is schematically illustrated in FIGS. 2(*a*) and 2(*b*). In FIG. 2(*a*) the bias voltage is greater than the collapse voltage whereby the membrane is collapsed before the pulses are applied. In FIG. 2(*b*) the membrane is biased in the snapback position before the AC voltage is applied. Operation of the membrane in response to applied pulses are capable of generating high frequency ultrasonic energy with high acoustic pressures.

Static finite element calculations to the cMUT FIG. 1 were performed using a commercially available FEM package (ANSYS 5.7) [ANSYS, INC., Southpointe, 275 Technology Drive, Canonsburg, Pa.] to model the membrane substrate contact. FEM elements were defined on the contacting surfaces as described in the following analysis. ANSYS standard element type, PLANE121, which features charge and voltage variables, and PLANE82, which features displacement and force variables, were used for electrostatic and structural analyses, respectively [ANSYS, INC., Southpointe, 275 Technology Drive, Canonsburg, Pa.]. The collapse of the membrane onto the substrate was modeled by means of contact-target pair elements (CONTA172 and TARGE169 [26]. These surface elements detected contact between the surfaces, and automatically applied the resulting contact forces. When contact occurred, the penetration of the surfaces and the forces due to the contact were calculated based on the material properties of $Si_3N_4$ used in the contacting surfaces of the membrane and the insulation layer. The surface elements were defined on both the bottom surface of the membrane and slightly above the insulation layer. The offset from the insulation layer which was included to re-mesh the gap when the structure was collapsed, was 5% of the gap in the analysis.

FEM was used to calculate the deflected membrane profile for applied bias voltage. The electrostatic-structural coupled solver, ESSOLV of ANSYS, was used to iterate automatically between the electrostatic and structural domains until the convergence criterion (based on both the electrostatic energy and maximum structural displacement in the model) was met. Collapse and snapback voltages were calculated with a relative error bound of 1%. A membrane under greater than the collapse voltage, collapsed, and an already collapsed membrane, under smaller than the snapback voltage, snapped back from the substrate.

Figure 3A:
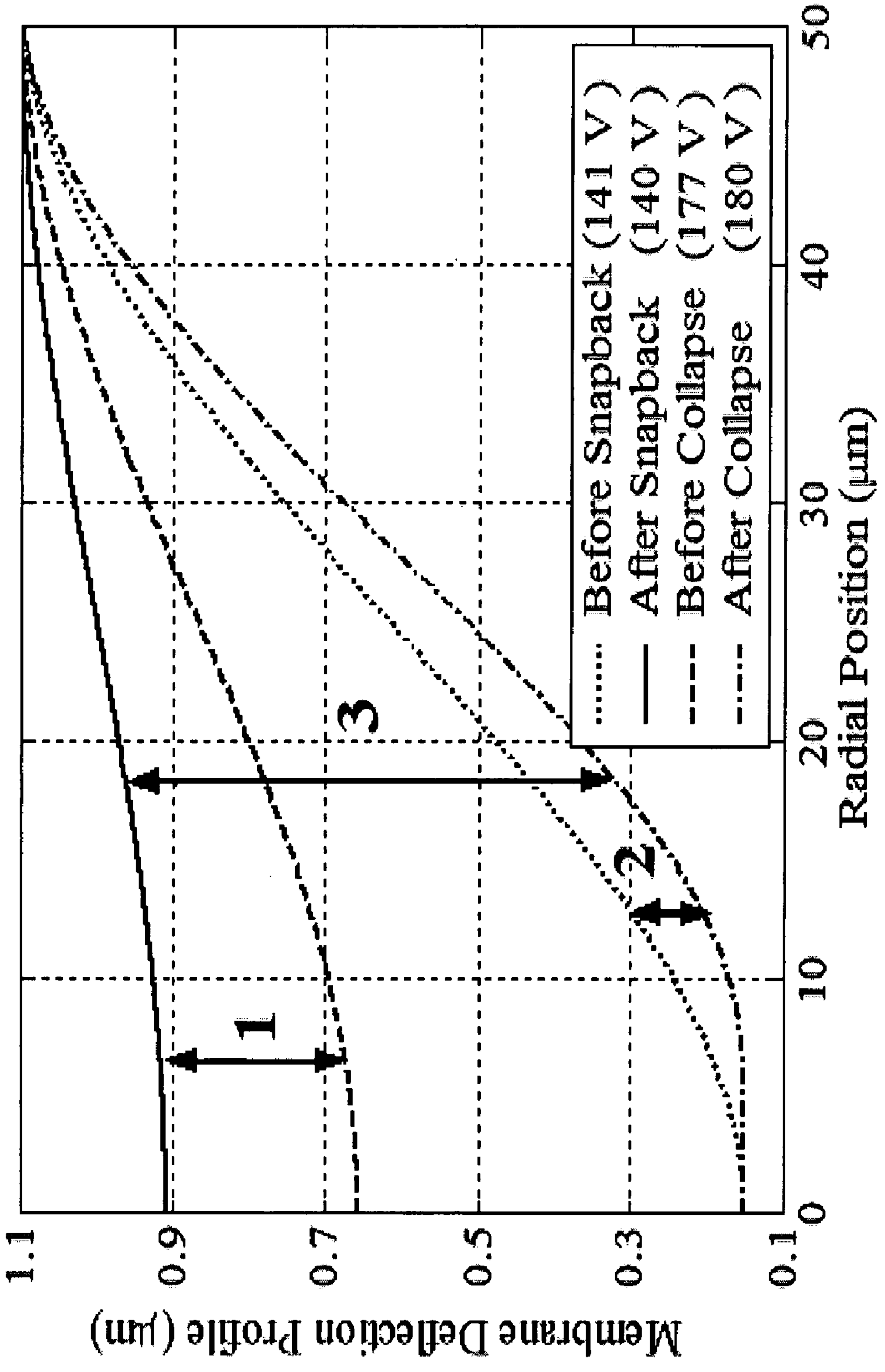
FIG. 3*a* shows the deflection profile of the cMUT shown in FIG. 1.
Figure 3B:
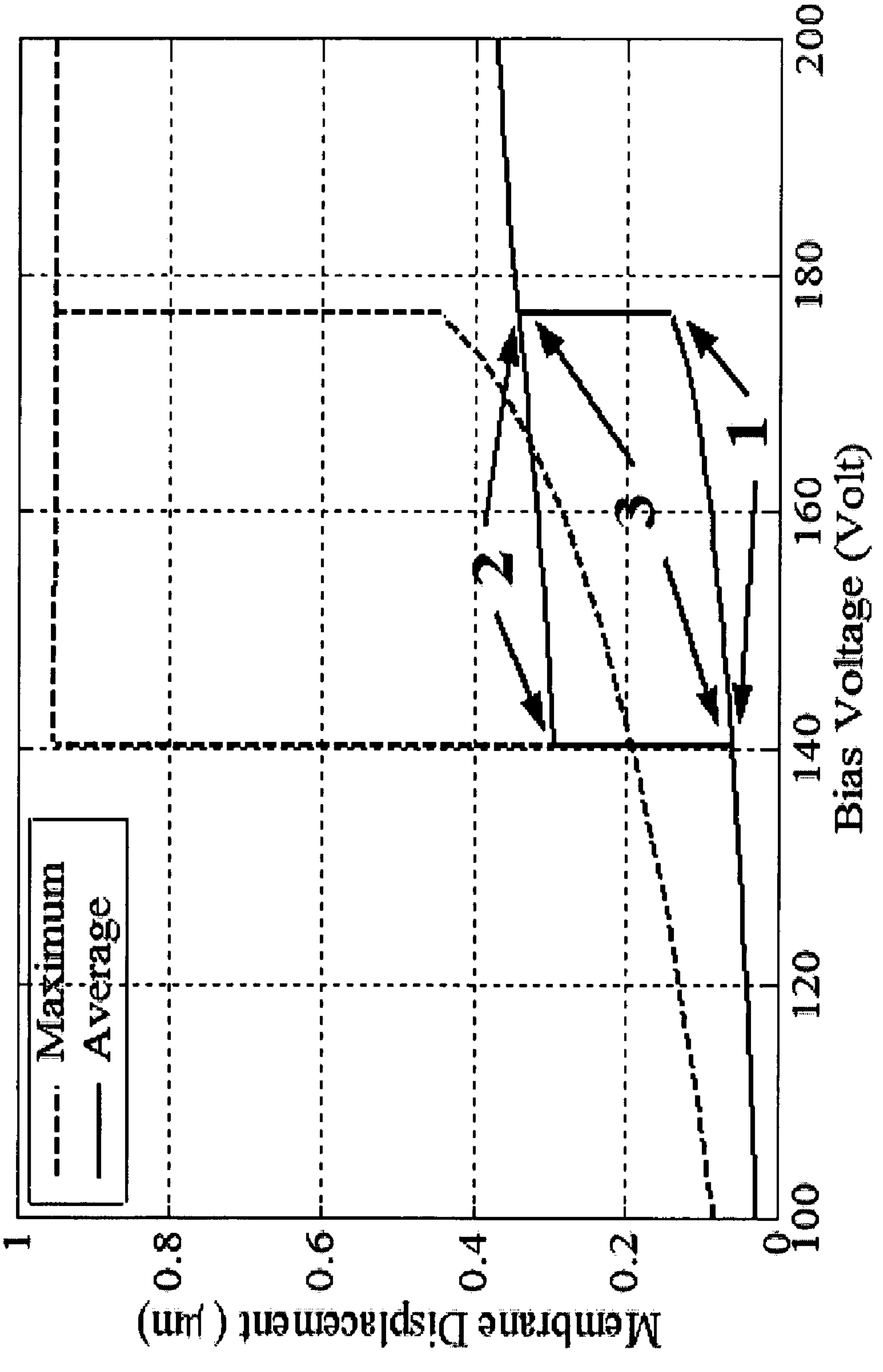
FIG. 3*b* shows the membrane displacement of the cMUT shown in FIG. 1.

Membrane deflection profiles of the cMUT about collapse and snapback voltages are depicted in FIG. 3(*a*). The infinitesimally thick electrode 17 ($t_e$=0 μm) was positioned on the top of the membrane 11 ($d_e$=1 μm). The electrode radius was half of the membrane radius ($r'_e=r_e/R=0.5$). The collapse and snapback voltages were 177 V and 140 V, respectively. The range of the membrane deflection profile (FIG. 3(*a*)) is well defined in the conventional ('1') and collapsed ('2') operation regimes, for applied voltages limited by the collapse and snapback voltages of the cMUT. However, the profiles at the collapse and snapback voltages were unstable; therefore, a slight voltage change above the collapse or below the snapback voltage caused the membrane to collapse, or the already collapsed membrane to snapback, respectively. The range of the membrane profile in the collapse-snapback operation ('3') was greater than the total range of the conventional and collapsed operation regimes combined.

The average and maximum membrane displacement of a cMUT ($r'_e$=0.5, $d_e$=1 μm) are depicted in FIG. 3(*b*). The net average displacement between the collapse and snapback voltages was 799 Å (22 Å/V) in the conventional ('1') and 524 Å (14 Å/V) in the collapsed ('2') operation regimes. The collapse-snapback operation yielded 2873 Å (70 Å/V) net average displacement. Thus, the displacement per volt of the cMUT was almost twice as great in the collapse-snapback operation as in the conventional and collapsed operations summed together.

In the collapse-snapback operation, 70 Å/V was calculated when the in-collapse and out-of-collapse voltages were equal to collapse and snapback voltages. If the operation was extended beyond these voltages, each additional volt contributed 22 Å/V and 14 Å/V in the conventional and collapsed regimes, respectively, reducing the displacement per volt below 70 Å/V. Therefore, maximum displacement per volt of the cMUT was achieved between collapse and snapback voltages. The specified voltages set the limit on the total displacement of the cMUT (2873 Å) in one collapse-snapback cycle for peak performance (70 A/V). Therefore, the cMUT should be designed for specific collapse and snapback voltages, to match the target acoustic output pressure (total membrane displacement in one cycle) of the ultrasonic application. In general, the total membrane displacement and the dynamic response of the cMUT in the collapse-snapback cycle determine the total acoustic output pressure. The static parameters of the cMUT (collapse and snapback voltages, total membrane displacement) were determined by static finite element calculations. These parameters were optimized for the above-mentioned criteria by adjusting the electrode parameters (electrode radius, thickness, and position).

A capacitive micromachined ultrasonic transducer consists of many cMUT cells. These cells, in general, can be of various shapes such as circular, square or hexagonal. The unit cell is used as the building block of the cMUT by periodic replication on the surface. In the following FEM analysis, a square membrane shape was used as the unit cell to cover the transducer area. The silicon membrane was supported on the edges with silicon oxide posts. There was a vacuum gap between the membrane and the substrate. A thin insulation layer of silicon oxide over the highly doped silicon substrate prevented shorting the ground electrode and the electrode on the bottom of the membrane in collapse. The ground electrode on the substrae was assumed to be at zero potential. The membrane was loaded with water.

Finite element methods (FEM) were used to analyze the cMUT using a commercially available FEM package (LS-DYNA) [Livermore Software Technology Corporation, Livermore Calif.]. LS-DYNA is a commercially available general-purpose dynamic FEM package, capable of accurately solving complex real world problems: fast and accurate, LS-DYNA was chosen by NASA for the landing simulation of space probe Mars Pathfinder. The public domain code that originated from DYNA3D, developed primarily for military and defense applications at the Lawrence Livermore National Laboratory, LS-DYNA includes advanced features, which were used in this FEM analysis: nonlinear dynamics, fluid-structure interactions, real-time acoustics, contact algorithms, and user-defined functions supported by the explicit time domain solver. This powerful, dynamic FEM package was modified for the accurate characterization of ultrasonic transducers on the substrate loaded with acoustic fluid medium.

Figure 4:
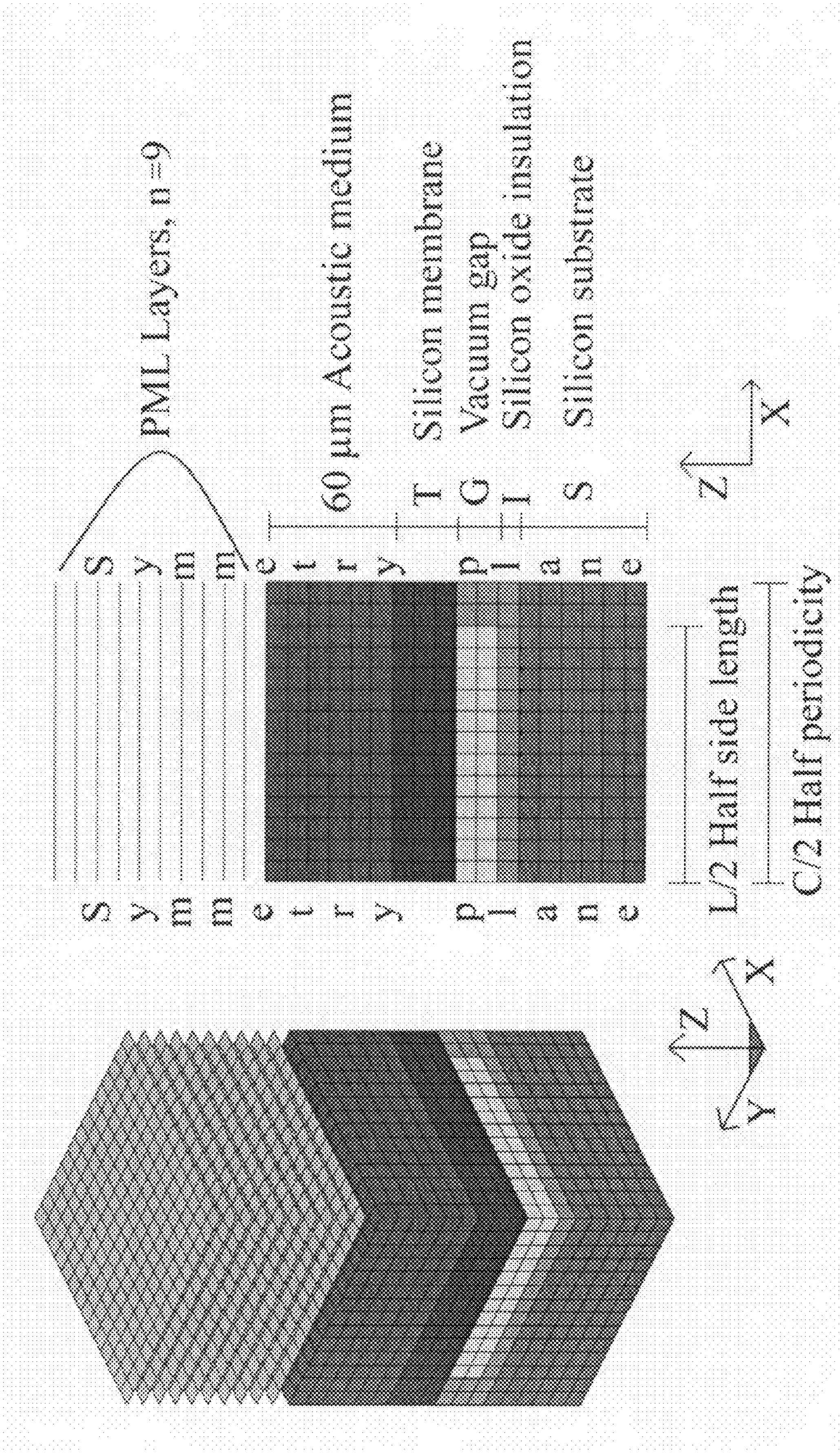
FIG. 4 schematically shows an FEM model of a cMUT used in the FEM analysis.

A FEM model of a cMUT is shown schematically in FIG. 4. Due to the symmetry of the square membrane, only a quarter of the membrane in the first quadrant of the cartesian coordinate (x>0, y>0) was modeled. Boundary conditions were applied as shown in FIG. 4. The planes x=0 and y=0 acted as symmetry planes. The x and y planes surrounding the model on the other side also acted as symmetry planes, since the adjacent membranes were identical. The symmetry planes allowed the motion of the corresponding nodes only in the plane. The substrate thickness (S) was 500 μm in the analysis. The membrane (T) was a silicon membrane. The vacuum gap (G) was established by a silicon oxide peripheral support. A silicon oxide isolation layer I was applied to the bottom substrate (S). The half periodicity was C/2 and half wide length of the vacuum gap was L/2. An acoustic medium A and PML layers are shown opposite the membrane.

TABLE I

PHYSICAL DIMENSIONS OF THE 2-D cMUT

| | |
|---|---|
| Side length (L) (μm) | 30 |
| Membrane thickness (T) (μm) | 1.2 |
| Gap thickness (G) (μm) | 0.18 |
| Insulating layer thickness (I) (μm) | 0.10 |
| Cell periodicity (c) (μm) | 35 |
| Substrate (5) (μm) | 500 |

Figure 5A:
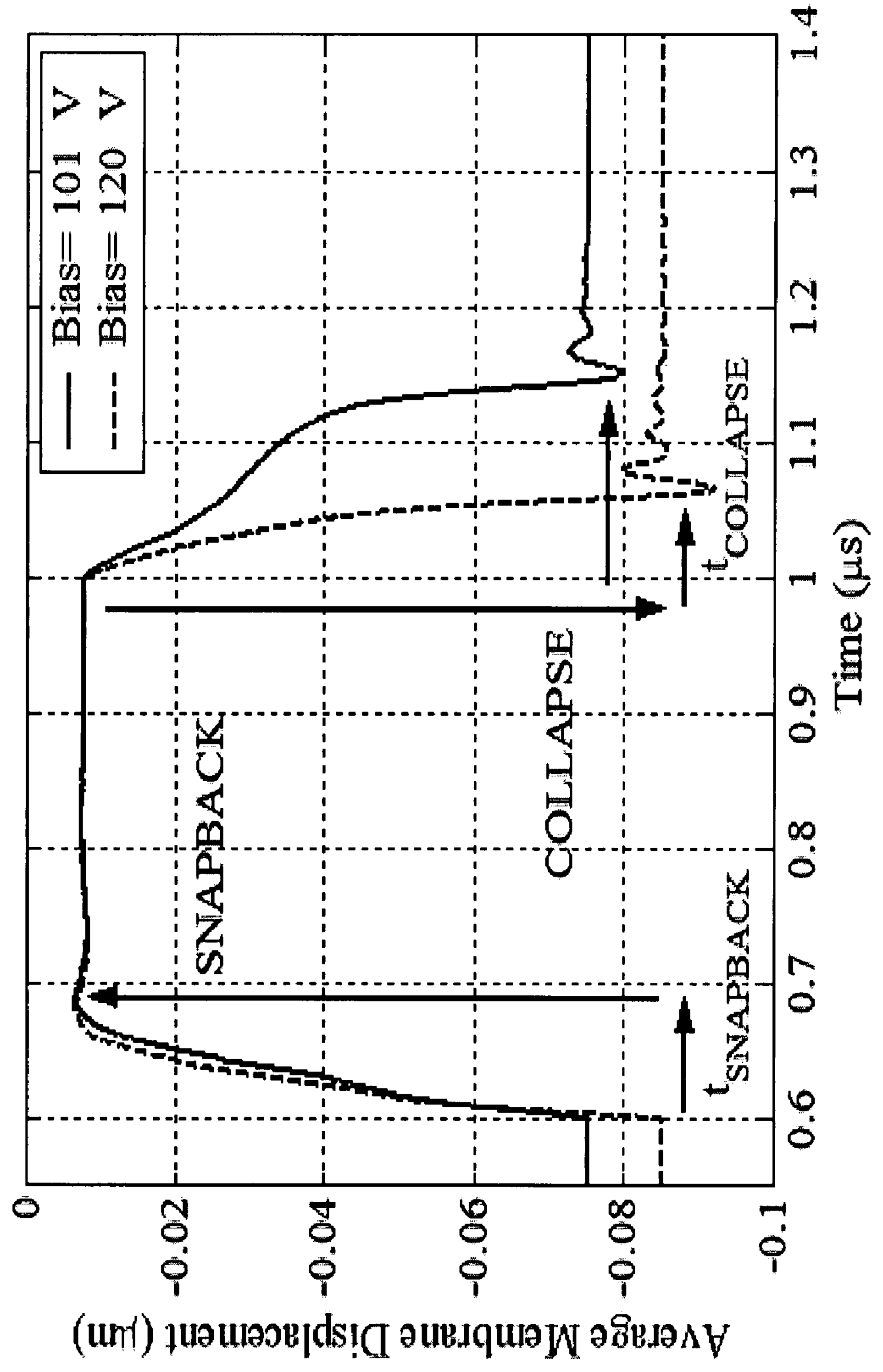
FIG. 5*a* shows the average displacement of the membrane of the cMUT shown in FIG. 3 as a function of time in collapsed-snapback operation.
Figure 5B:
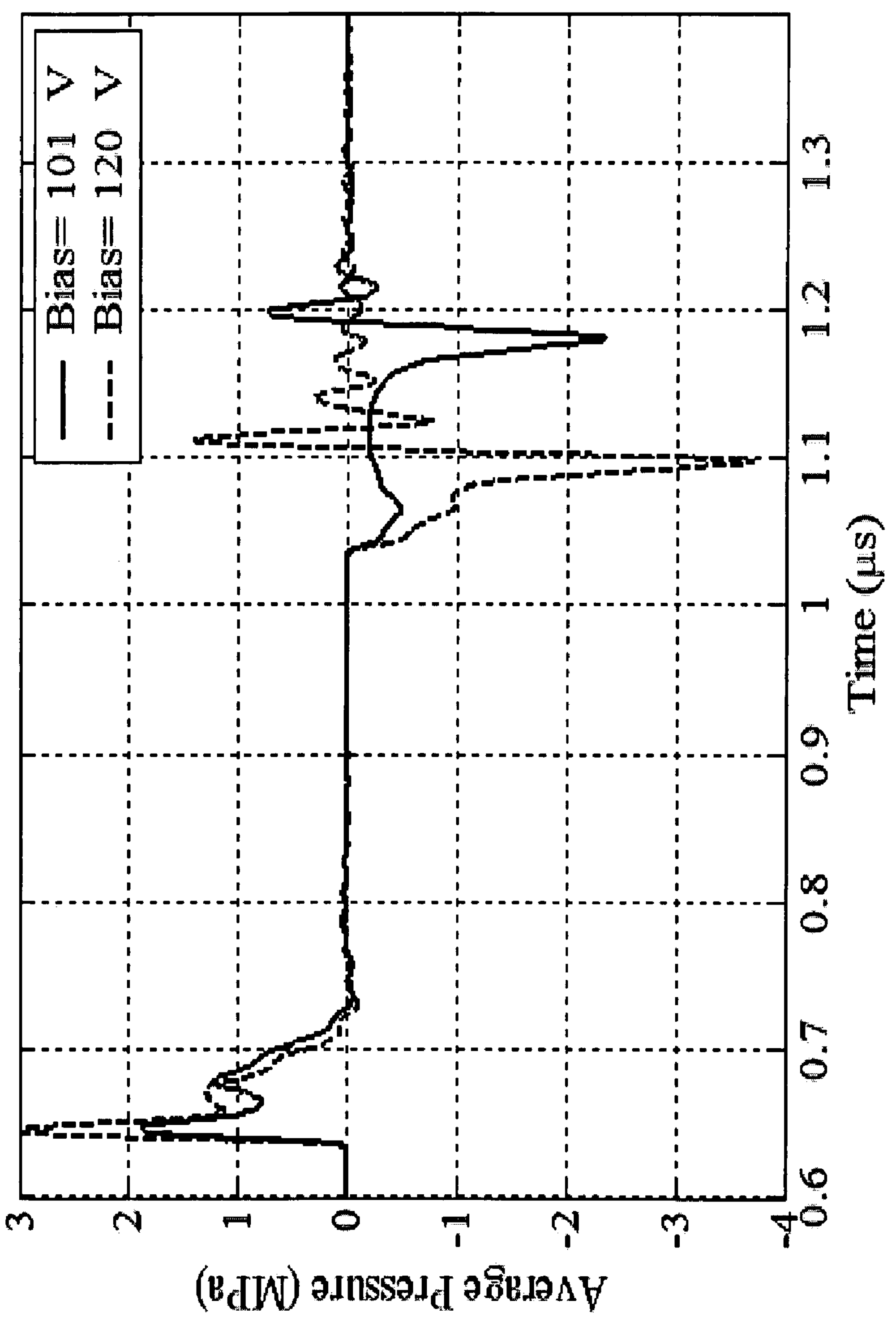
FIG. 5*b* shows the average pressure of the membrane of the cMUT shown in FIG. 3 as a function of time in collapsed-snapback operation.

The 2-D infinite cMUT described with reference to FIG. 4 and with the physical dimensions given in Table I had collapse and snapback voltages of 96 V and 70 V, respectively. A cMUT membrane subject to voltages greater than the collapse voltage will collapse. A collapsed membrane will snapback if the applied voltage is less than the snapback voltage. However, the time that it takes for the membrane to collapse ($t_{COLLAPSE}$) or for the already collapsed membrane to snapback ($t_{SNAPBACK}$) will determine the dynamic response of the cMUT. The average membrane displacement of a cMUT in the collapse-snapback operation regime is depicted in FIG. 5(*a*). The solid line represents this operation when the applied voltage was changed from 101 V in collapse to 65 V out of collapse. Initially, the membrane was biased in collapse by applying 101 V (5 V above the collapse voltage). The average membrane displacement was −751 Å. At t=0.6 μs, the voltage was changed to 65 V (5 V below the snapback voltage). The average membrane displacement crossed the static membrane displacement value of −77 Å, corresponding to the applied voltage of 65 V, at t=0.678 μs. The snapback time ($t_{SNAPBACK}$) was 78 ns. The net membrane displacement was 674 Å. At t=1 μs, the voltage was changed back to 101 V. The average membrane displacement crossed the static membrane displacement value of −751 Å, corresponding to the applied voltage of 101 V, at t=1.146 μs. The collapse time ($t_{COLLAPSE}$) was 146 ns.

One way to reduce the collapse time for this cMUT design was increasing the applied voltage for collapsing the membrane. The dashed line represents the same operation when the applied voltage was changed to 120 V in collapse to 65 V out of collapse. The average membrane displacement was −852 Å in collapse. At t=0.6 μs, the voltage was changed to 65 V (5 V below the snapback voltage). The average membrane displacement crossed the static membrane displacement value of −77 Å, corresponding to the applied voltage of 65 V, at t=0.667 μs. The snapback time ($t_{SNAPBACK}$) was 67 ns. The net membrane displacement was 775 Å. At t=1 μs, the voltage was changed back to 120 V (24 V above the collapse voltage). The average membrane displacement crossed the static membrane displacement value of −852 Å, corresponding to the applied voltage of 120 V, at t=1.062 μs. The collapse time ($t_{COLLAPSE}$) was 62 ns. Remarkable reduction (60%) in the collapse time and 15% increase in the net membrane displacement were achieved by only 20% increase in the collapsing voltage of the collapse-snapback operation.

Average acoustic output pressures of the collapse-snapback operations (101-65 V and 120-65 V) are depicted in FIG. 5(*b*). Acoustic output pressure was averaged over the plane 60 μm away from the cMUT surface. Snapback and collapse half-cycles of 101-65 V generated 1.9 MPa and −2.35 MPa peak acoustic output pressures, respectively. Snapback and collapse half-cycles of 120-65 V generated 2.98 MPa and −3.7 MPa peak acoustic output pressures, respectively. The peak acoustic output pressure magnitude generated in the snapback half-cycle was 80% of that generated in the collapse half-cycle for both 101-65 V and 120-65 V collapse-snapback operations.

Figure 6A:
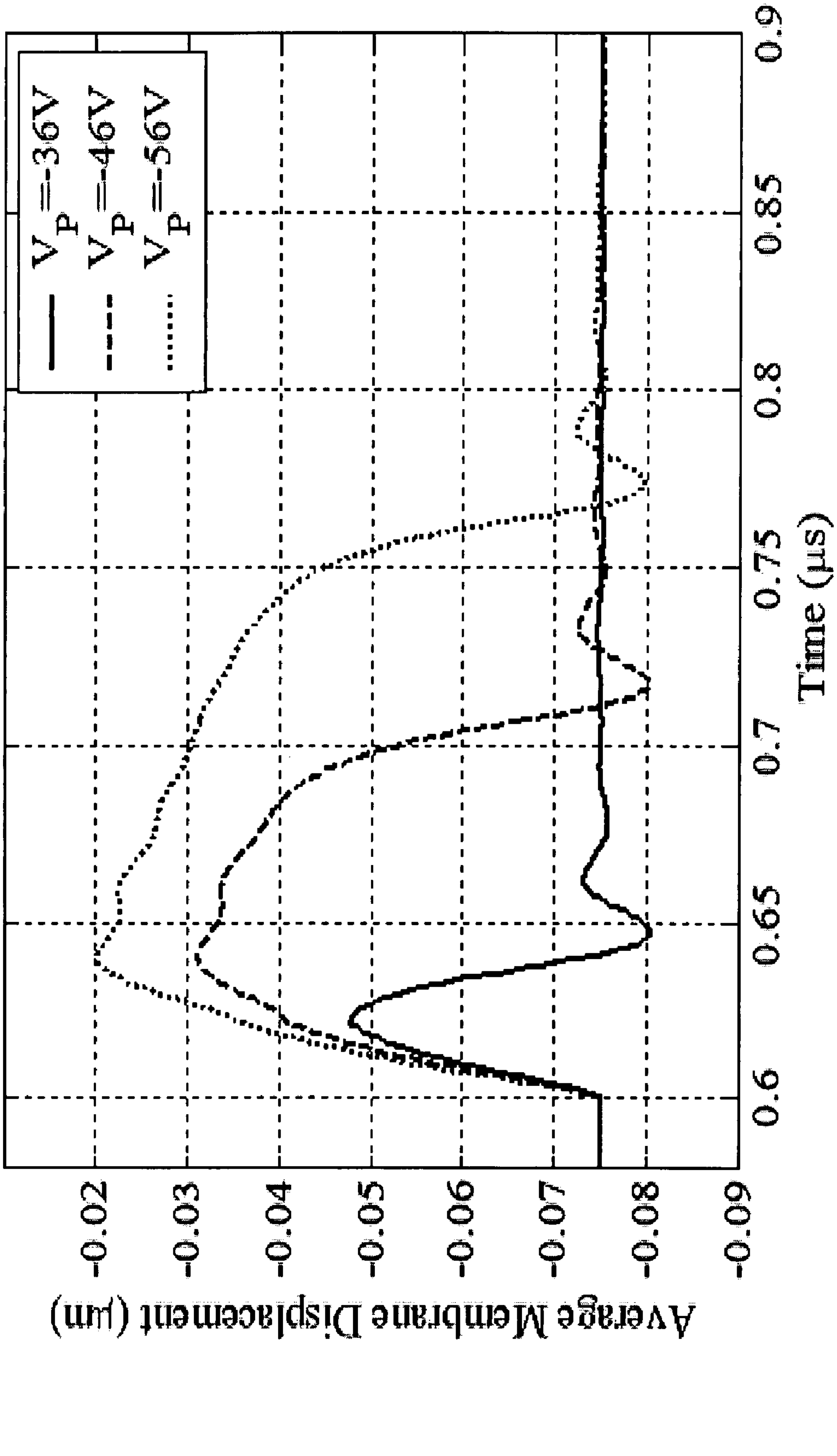
FIGS. 6*a, b,* and *c* show a) average membrane displacement as a function of time, b) average pressure as a function of time, and c) the frequency spectrum of the average acoustic output pressure divided by the spectrum of the pulse for collapsed-snapback operation-of the cMUT shown in FIG. 3 with different pulse excitation voltages at a one bias voltage.
Figure 6B:
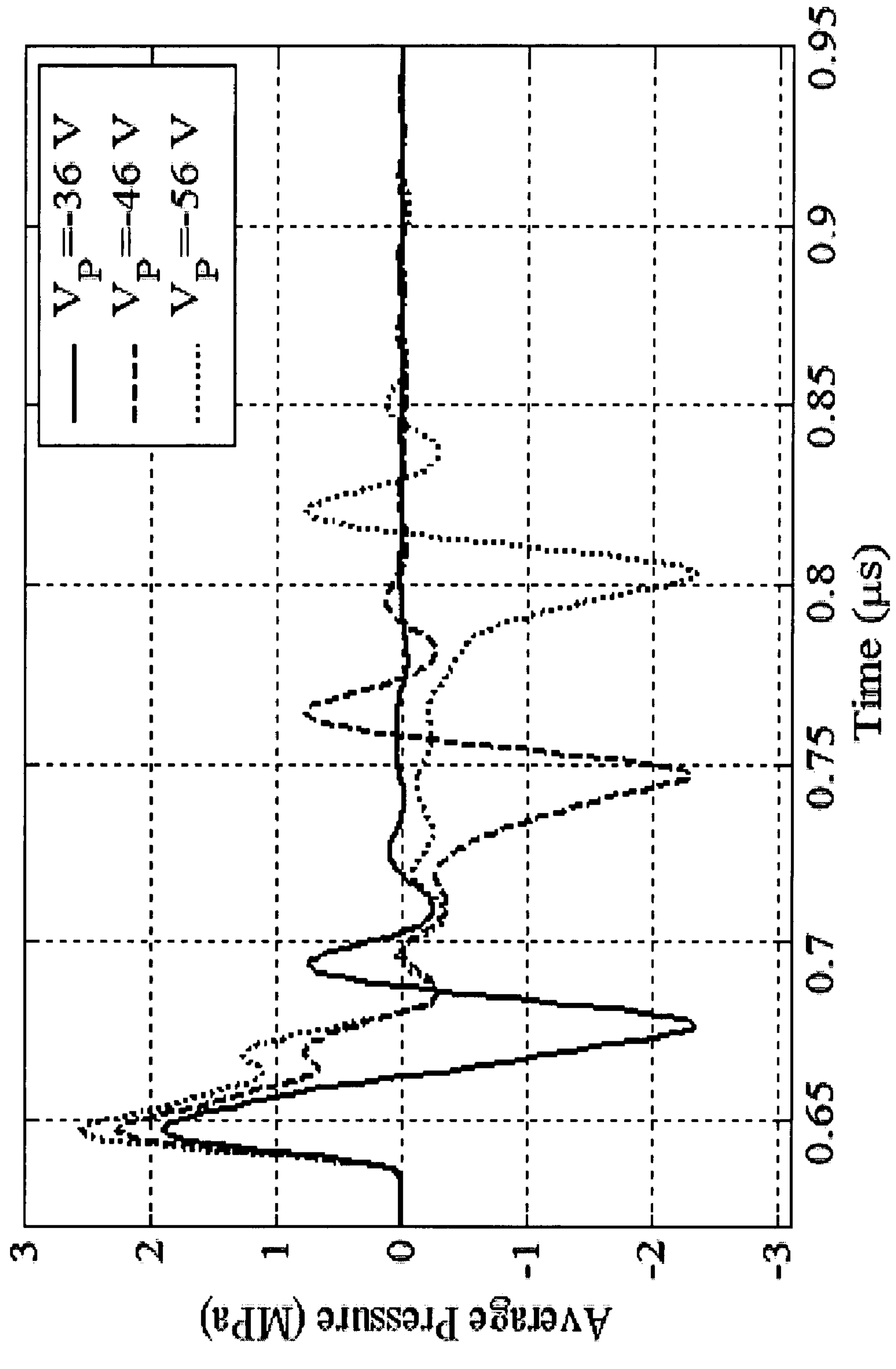
Figure 6C:
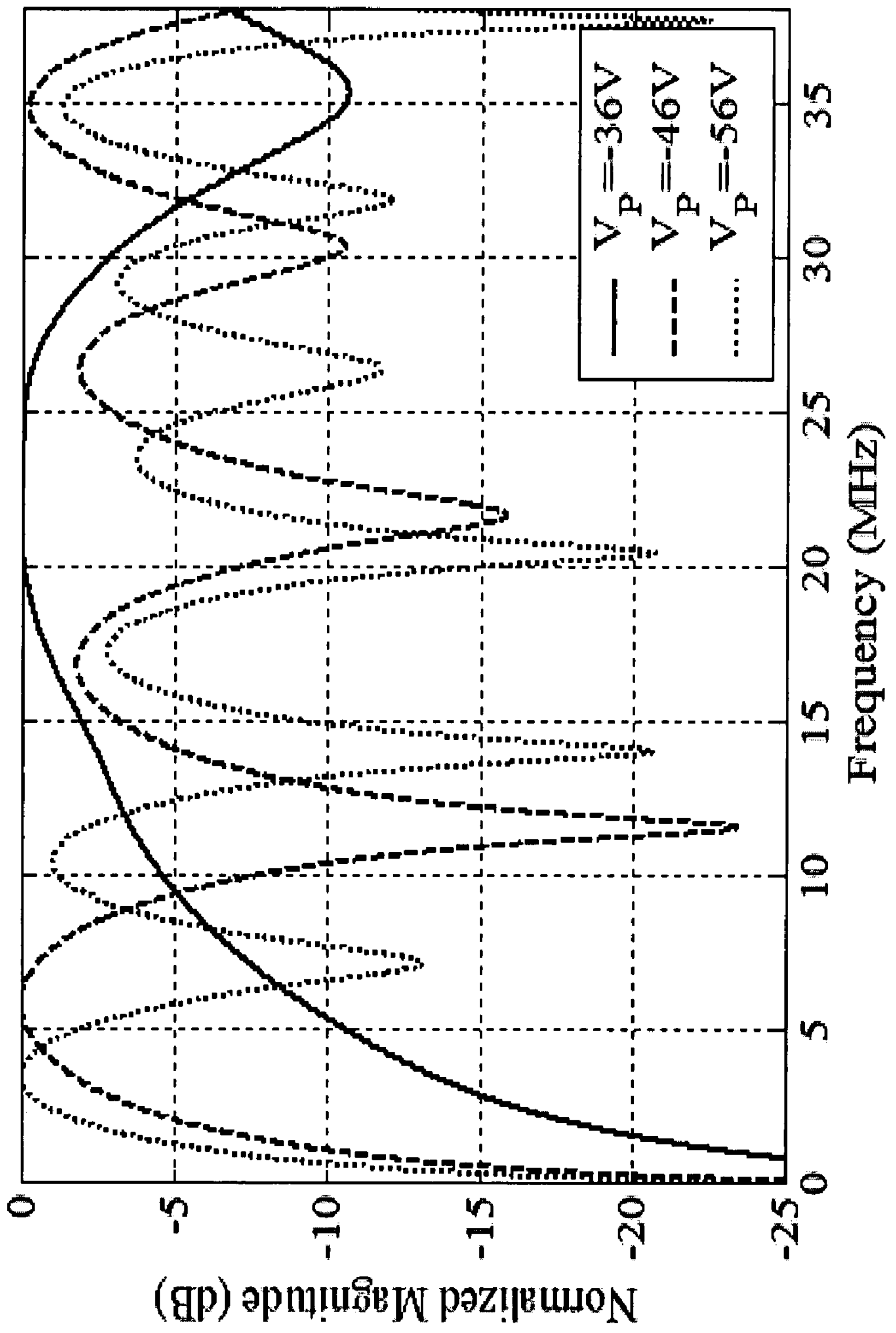

The collapse and snapback times ($t_{COLLAPSE}$ and $t_{SNAPBACK}$) were determined by applying step voltages as described above. A cMUT, biased with 101 V in collapsed operation regime, was excited with the rectangular pulses of −36 V, −46 V and −56 V for $t_P$=20 ns. The average membrane displacement time waveforms are shown in FIG. 6(*a*). The solid line represents −36 V pulse, where peak net membrane displacement of 273 Å was reached at t=0.622 μs, and the equilibrium membrane displacement of −751 Å was crossed at t=0.641 μs. The dashed line represents −46 V pulse, where peak net membrane displacement of 441 Å was reached at t=0.640 μs, and the equilibrium membrane displacement of −751 Å was crossed at t=0.711 μs. The dotted line represents −56 V pulse, where peak net membrane displacement of 549 Å was reached at t=0.640 μs, and the equilibrium membrane displacement of −751 Å was crossed at t=0.768 μs. The net average membrane displacements per volt were calculated as 7.6 Å/V, 9.6 Å/V and 9.8 Å/V for −36 V, −46 V and −56 V pulse amplitudes, respectively. The total of collapse and snapback times for −36 V, −46 V and −56 V pulses were 41 ns, 111 ns and 168 ns, respectively.

Average acoustic output pressures of the collapse-snapback operations are depicted in FIG. 6(*b*). Acoustic output pressures were averages over the plane 60 μm away from the cMUT surface. Snapback half-cycles of −36 V, −46 V and −56 V pulses generated 1.9 MPa, 2.26 MPa and 2.56 MPa, respectively. Collapse half-cycles of these pulses generated −2.33 MPa, with less than 2% variation for all pulse amplitudes (−36V, −46 V and −56 V). The frequency spectrums of the average acoustic pressures were divided with those of the pulses (FIG. 5(*c*)). The collapse-snapback operation of −36 V pulse had 80% fractional bandwidth at the center frequency of 21.6 MHz. A larger pulse of −46 V changed the fractional bandwidth to 100% at the center frequency of 5.95 MHz.

Figure 7A:
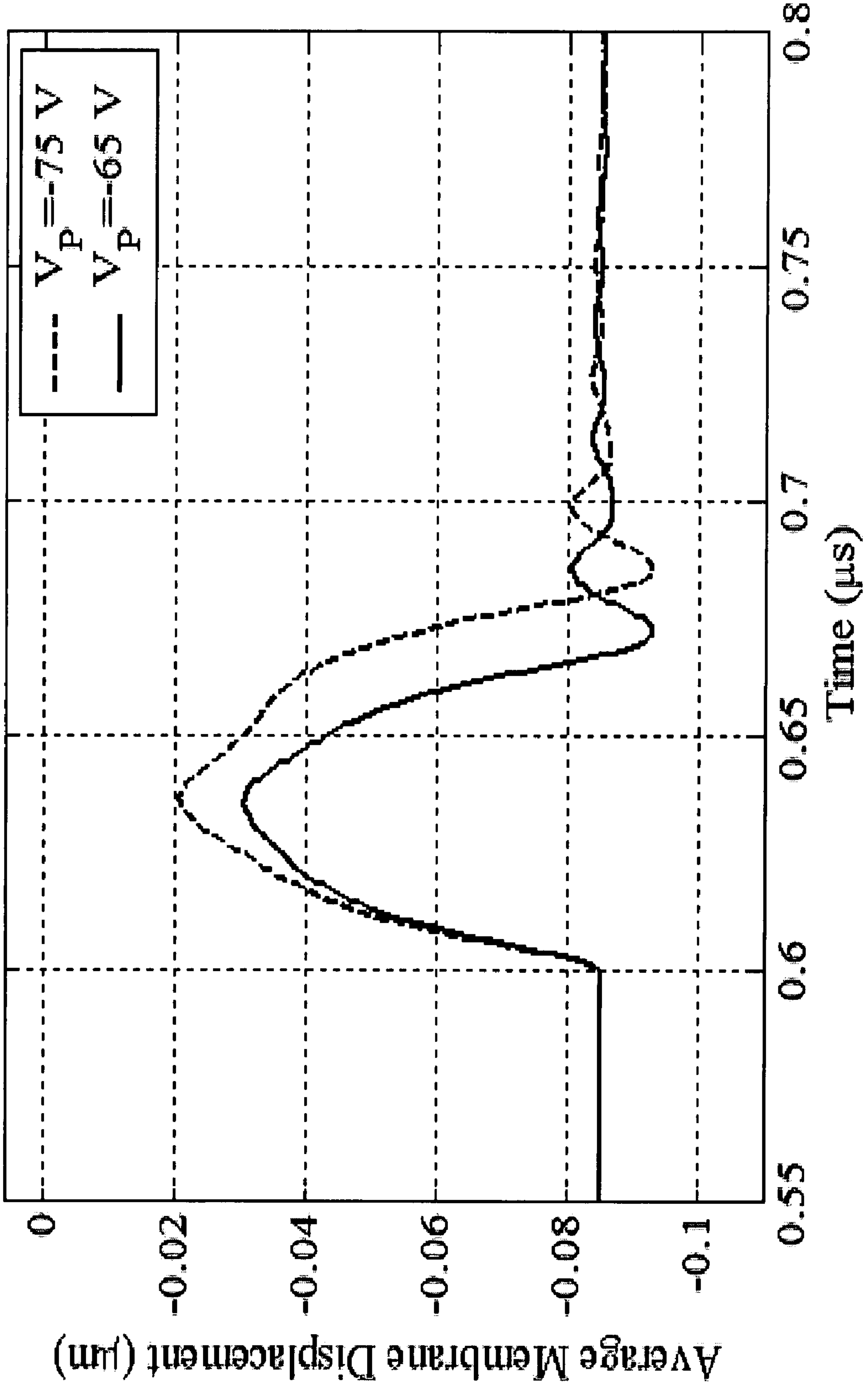
FIGS. 7*a, b,* and *c* show a) average membrane displacement as a function of time, b) average pressure as a function of time, and c) the frequency spectrum of the average acoustic output pressure divided by the spectrum of the pulse for collapsed-snapback operation of the cMUT shown in FIG. 3 with different pulse excitation voltages at another bias voltage.
Figure 7B:
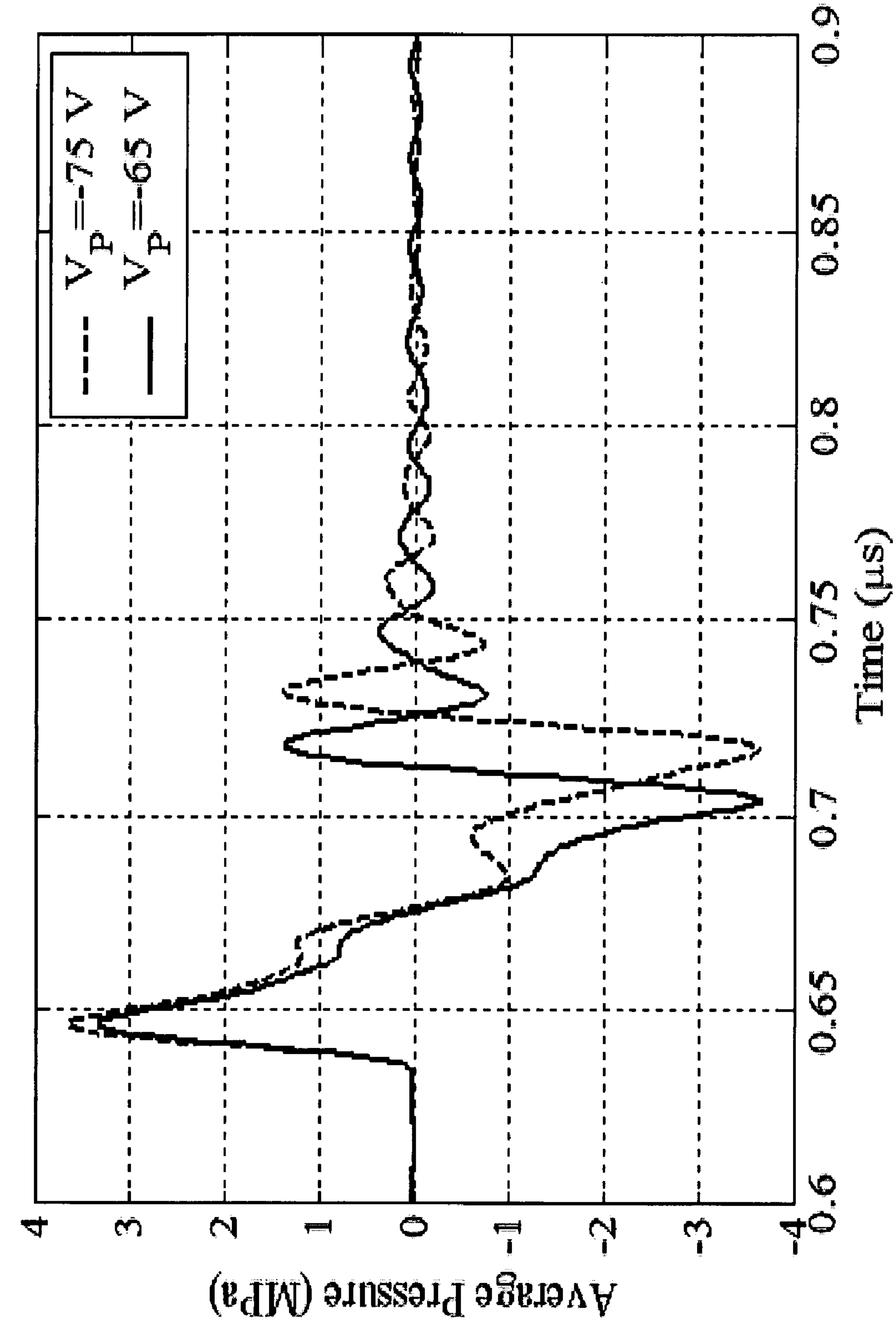
Figure 7C:
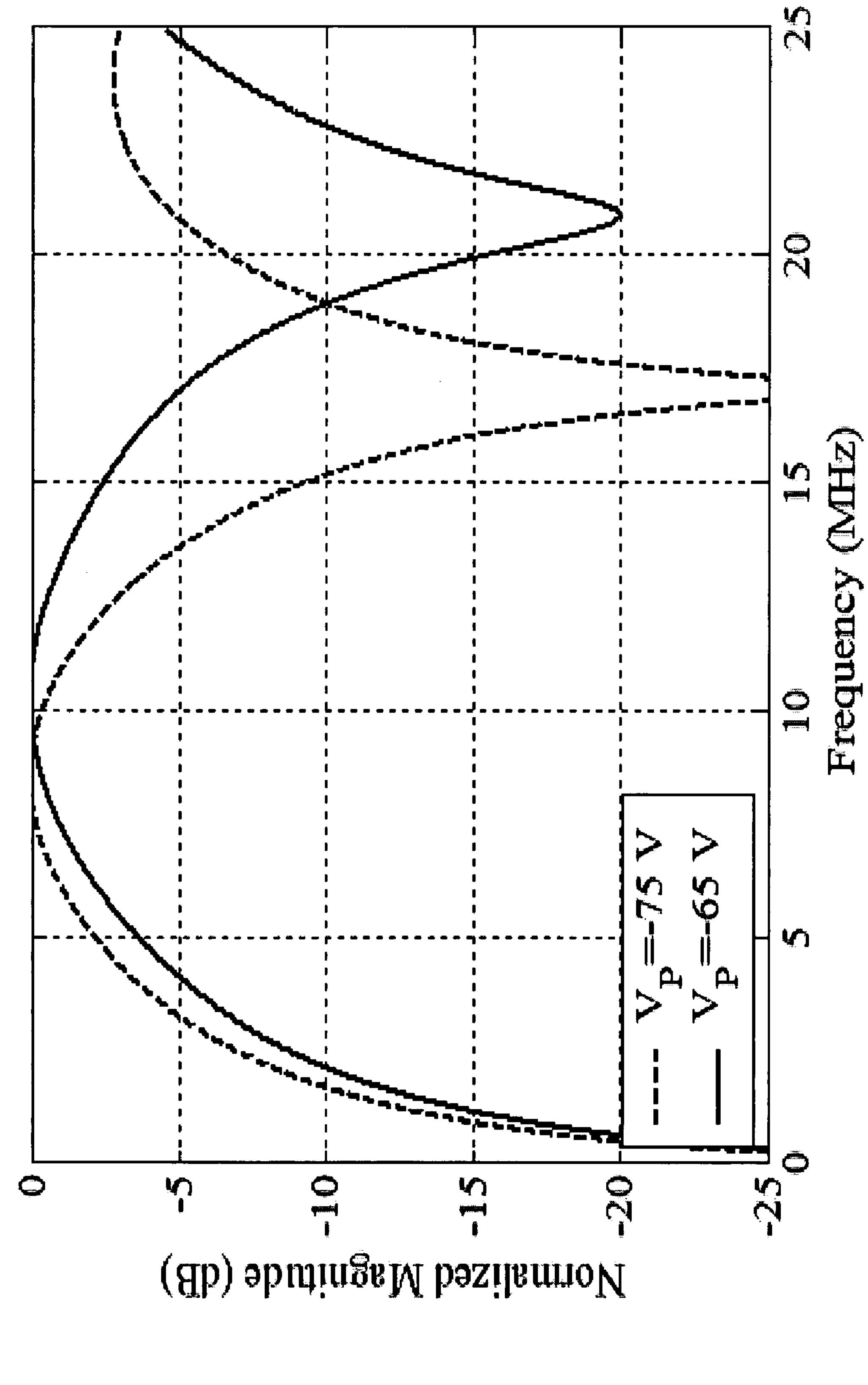
Figure 8A:
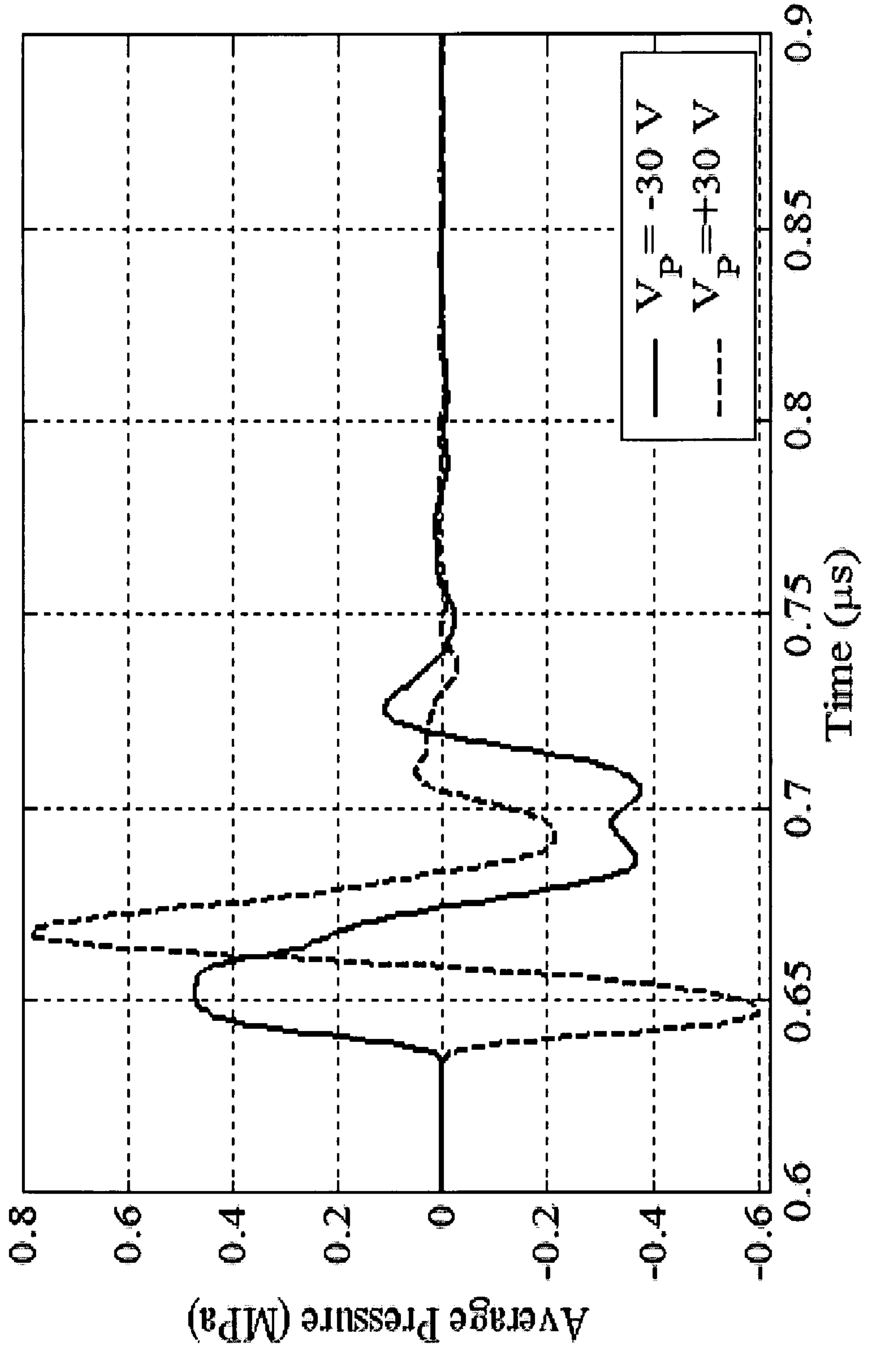
FIGS. 8*a, b, c* and *d* and show a) Average pressure as a function of time. The solid line corresponds to −30 V rectangular pulse excitation and the dashed line corresponds to the opposite polarity +30 V excitation; b) The frequency spectrum of the average acoustic output pressure divided by the spectrum of the pulse. The peak of the resulting spectrum is normalized to 0 dB; c) Average pressure as a function of time. The frequency spectrum of the average acoustic output pressure divided by the spectrum of the pulse.
Figure 8B:
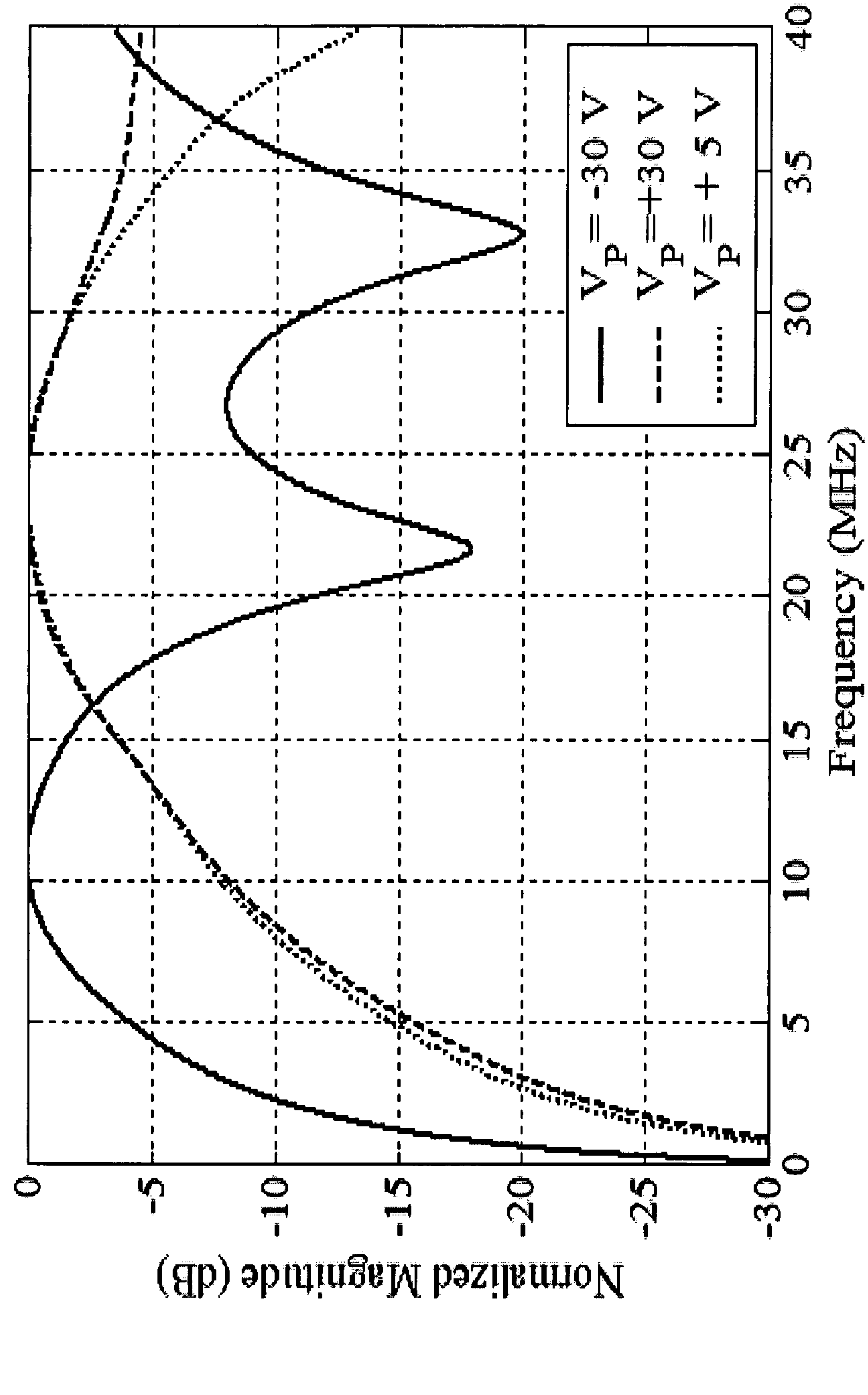
Figure 8C:
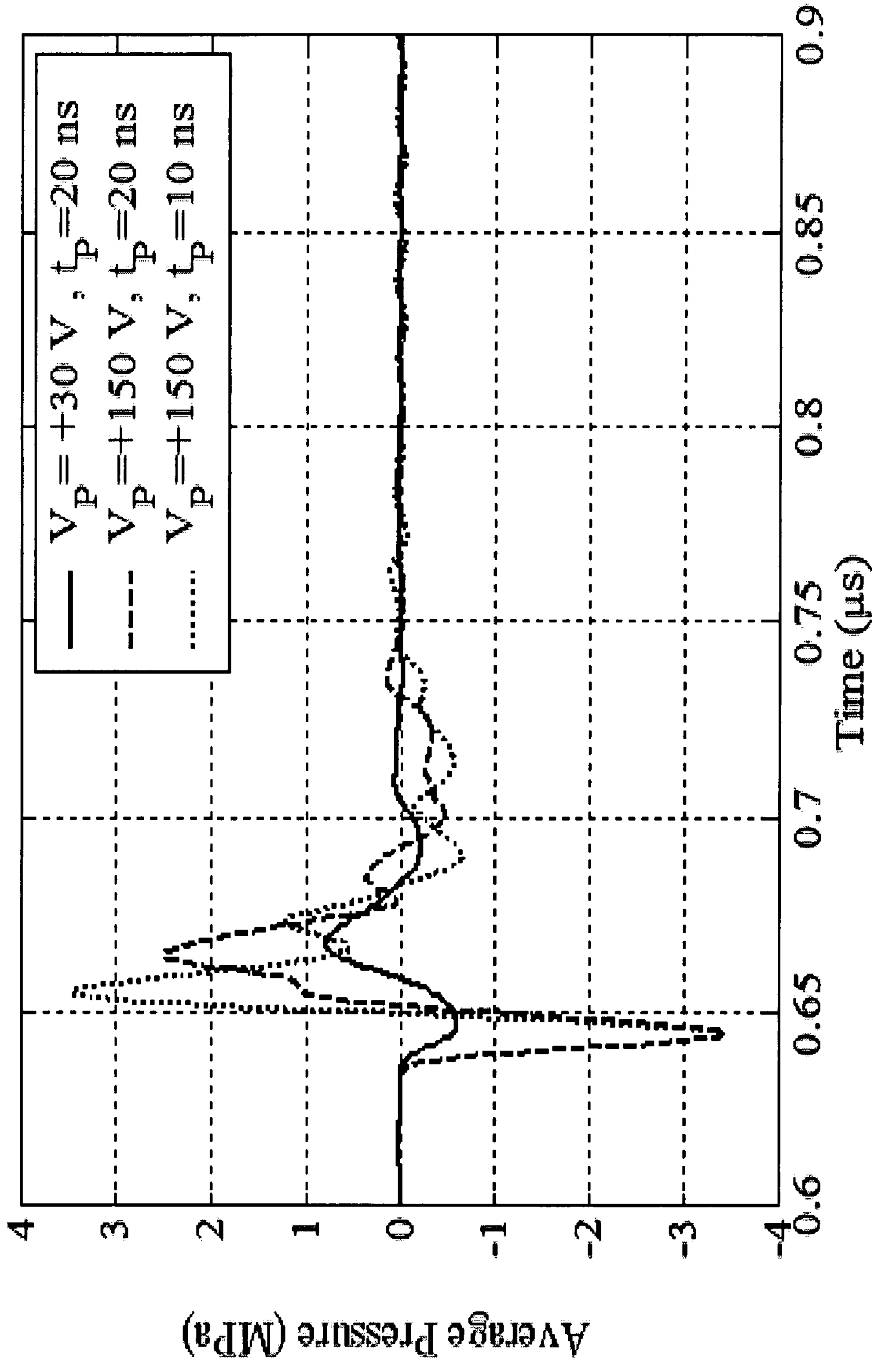
Figure 8D:
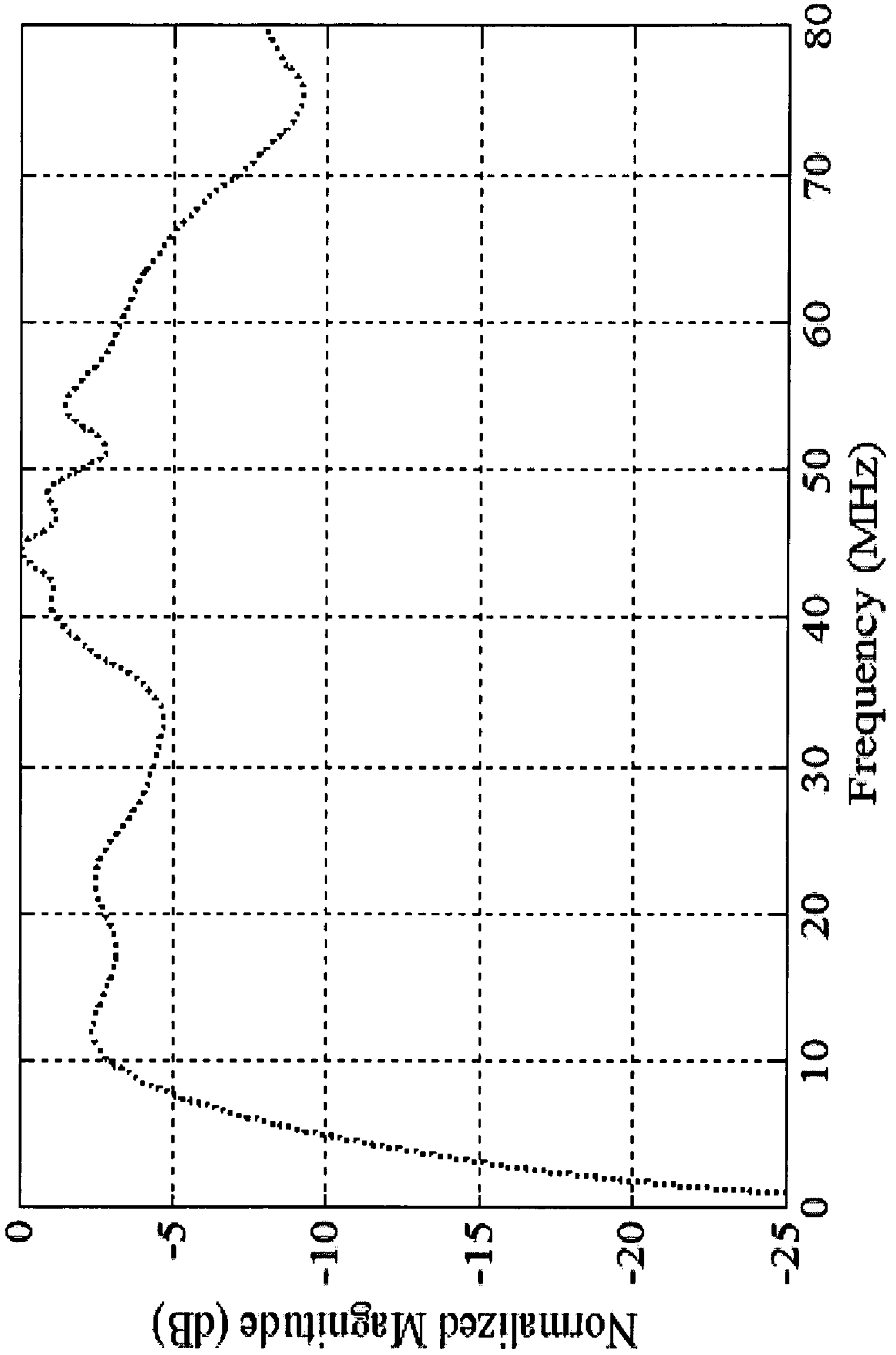
Figure 9A:
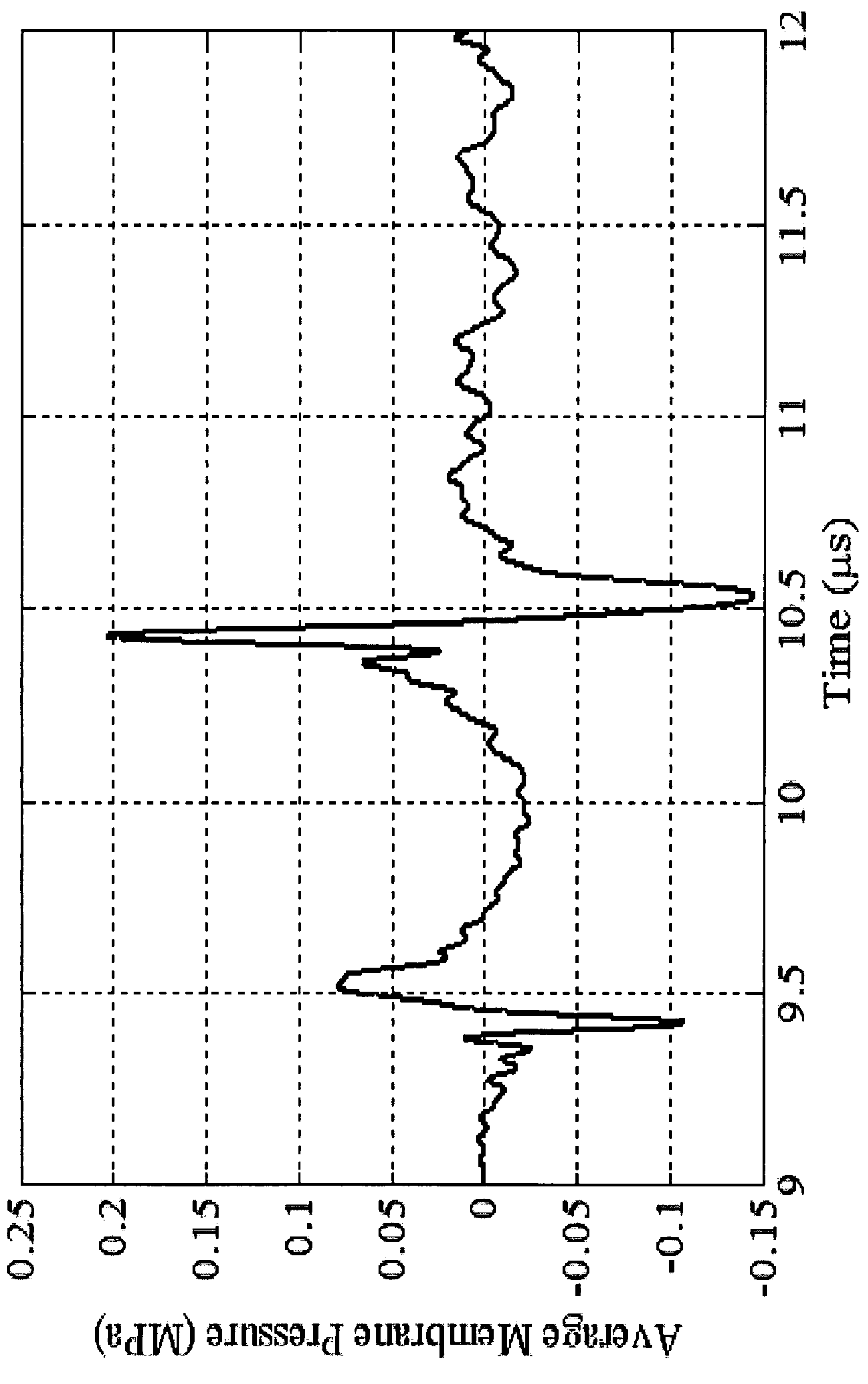
FIG. 9(*a*) is a diagram showing experimental results in the form of a graph of Average Membrane Pressure (MPa) versus Time (μs).
Figure 9B:
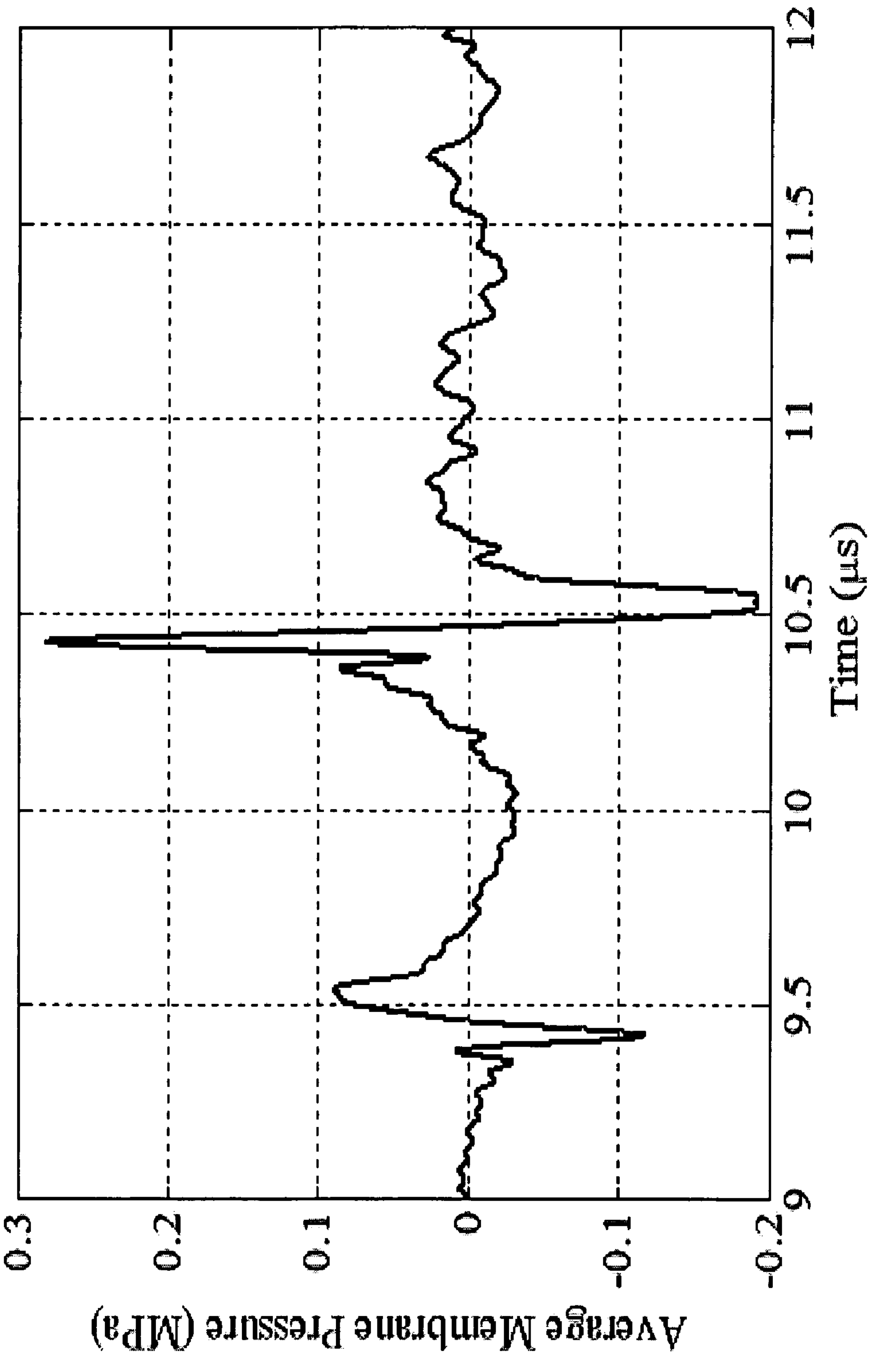
Figure 9C:
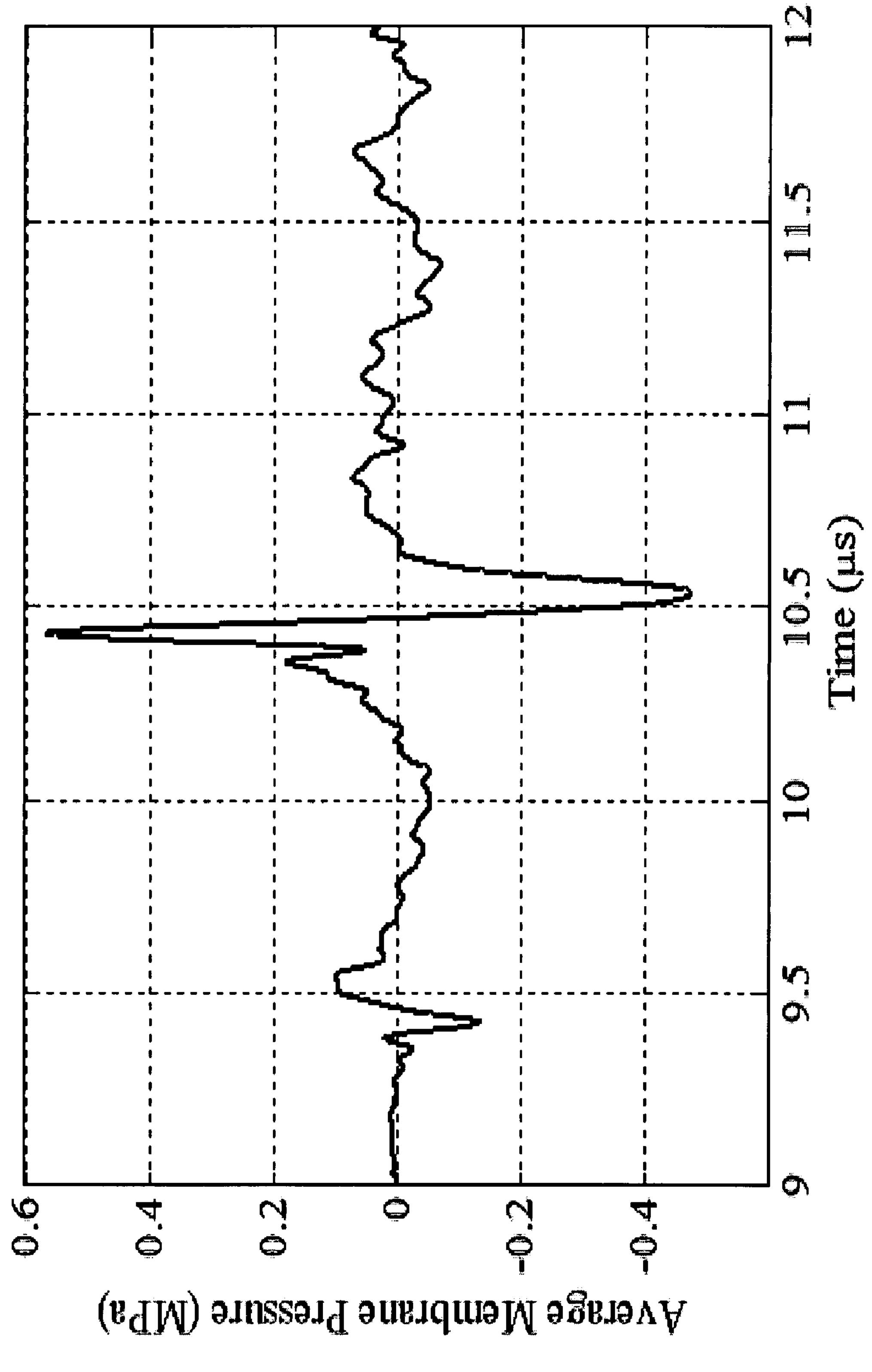
Figure 9D:
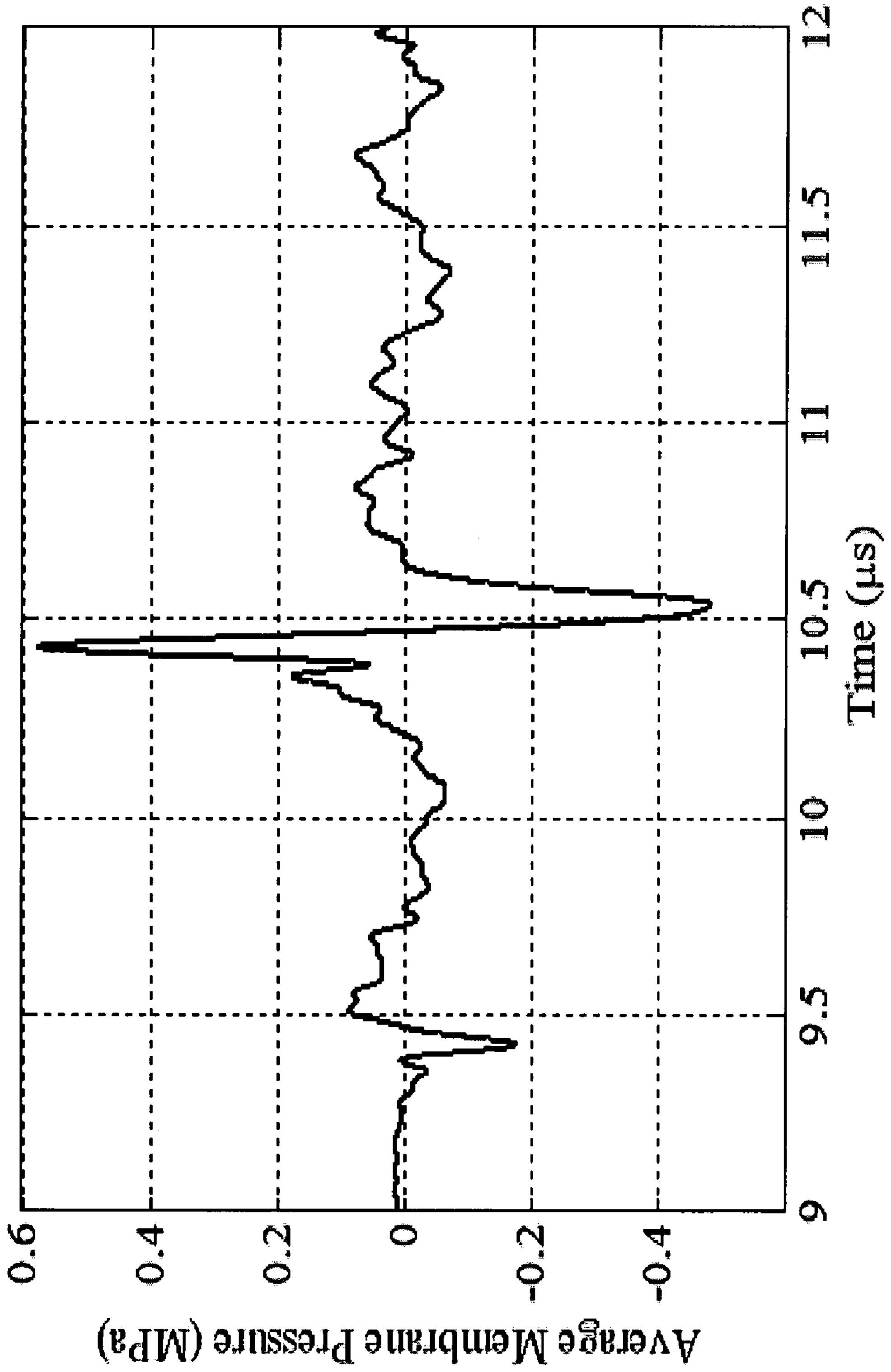

The collapse-snapback operation of the cMUT was analyzed with pulses applied on a membrane biased at 101 V. The collapse time ($t_{COLLAPSE}$) limited the center frequency of the acoustic output pressure to less than 6 MHz for pulse amplitudes larger than 46 V. In order to decrease the collapse time, the collapsing voltage of the collapse-snapback operation was increased. The cMUT, biased with 120 V (125% of the collapse voltage) in collapsed operation regime, was excited with the rectangular pulses of −65 V and −75 V for $t_P$=20 ns. The average membrane displacement time waveforms are shown in FIG. 7(*a*). The solid line represents −65 V pulse, where peak net membrane displacement of 547 Å (8.4 Å/V) was reached at t=0.636 μs and the equilibrium membrane displacement of −852 Å was crossed at t=0.667 μs. The dashed line represents −75 V pulse, where peak net membrane displacement of 645 Å (8.6 Å/V) was reached at t=0.637 μs and the equilibrium membrane displacement of −852 Å was crossed at t=0.681 μs.

Average acoustic output pressures of the collapse-snapback operations are depicted in FIG. 7(*b*). Acoustic output pressures were averaged over the plane 60 μm away from the cMUT surface. Snapback half-cycles of −65 V and −75 V pulses generated 3.34 MPa and 3.64 MPa, respectively. Collapse half-cycles of these pulses generated −3.64 MPa, with less than 1% variation for both pulse amplitudes (−65 V and −75 V). The peak-to-peak pressures of 6.98 MPa and 7.28 MPa were calculated, yielding 107 kPa/V and 97 $k_{Pa/V}$ acoustic output pressure per volt for 65 V and 75 V pulse amplitudes, respectively. The frequency spectrums of the average acoustic pressures were divided by those of the pulses (FIG. 7(*c*)). The collapse-snapback operation of −65 V pulse had 97% fractional bandwidth at the center frequency of 10.4 MHz. A larger pulse of −75 V pulse had 96% fractional bandwidth at the center frequency of 8.5 MHz.

In the above calculations, high acoustic output pressures (100 kPa/V) were achieved at the center frequency of 10 MHz for the cMUT with the physical dimensions given in Table I. However, the center frequency was sensitive to the pulse amplitude. Increasing the collapsing voltage to decrease the collapse time was one way of reducing this pulse amplitude sensitivity of the center frequency. Another way is to design the cMUT with equal collapse and snapback voltages, so that the electrostatic pressure on the membrane changes more smoothly during the collapse-snapback operation. The existing cMUT dimensions were modified as follows: the gap (G) was changed from 0.18 μm to 0.1 μm and the insulation layer thickness (I) was changed from 0.1 μm to 0.37 μm. The other dimensions, listed in Table I, were kept unchanged. This new cMUT design featured collapse and snapback voltages both equal to 92 V. In the following calculations, this design was analyzed in terms of the center frequency, the fractional bandwidth and the acoustic output pressure.

The cMUT, biased with 100 V (108% of the collapse voltage) in collapsed operation regime, was excited with the rectangular pulses of −30 V (collapse-snapback operation) and +30 V (collapsed operation). Average acoustic output pressures of these operations are depicted in FIG. 8(*a*). The fully closed gap between the membrane center and the substrate opened for −30 V pulse, resulting in collapse-snapback operation. Peak pressures of 472 kPa in the snapback and −368 kPa in the collapse half-cycles were calculated, yielding 28 kPa/V average output pressure per volt. The contact between the membrane and the substrate was always present in the pulse excitation of +30 V, and therefore, the cMUT operated in the collapsed regime. Peak-to-peak pressure of 1.38 MPa was calculated, yielding 46 kPa/V average acoustic output pressure per volt. The frequency spectrums of the average acoustic pressures were divided by those of the pulses (FIG. 8(*b*)). The collapse-snapback operation of −30 V pulse had 98% fractional bandwidth at the center frequency of 10.8 MHz. The collapsed operation of +30 V pulse had 71% fractional bandwidth at the center frequency of 23.7 MHz. The small signal (+5 V) pulse excitation in the collapsed operation of the cMUT had similar center frequency (24 MHz) and fractional bandwidth (66%).

The cMUT, biased with 100 V, operated in the collapsed regime when excited with +30 V pulse for $t_P$=20 ns. However, when the cMUT was excited with a +150 V pulse for $t_P$+20 ns, the membrane and the substrate lost contact, and thus, operated in the collapse-snapback regime (FIG. 8(*c*)). Peak-to-peak pressure of 5.9 MPa was calculated, yielding 39 kPa/V average output pressure per volt. Due to the shift of the center frequency to higher frequencies, the pulse duration ($t_P$) was decreased to 10 ns. Average output pressure of 6.8 MPa (45 kPa/V) was calculated for this excitation. The frequency spectrum of the average acoustic pressure (+150 V pulse for $t_P$=10 ns) was divided by that of the pulse (FIG. 8(*d*)). The collapse-snapback operation of +150 V pulse had 150% 5-dB fractional bandwidth at the center frequency of 37 MHz.

The collapse-snapback operation is described above. The important finding is the generation of large acoustic output pressures (7 MPa) by large signal-excitation. Although this operation is highly nonlinear, it is possible to find a set of bias voltage (120 V), pulse amplitude (55 V), and pulse duration (20 ns) to generate acoustic output pressure at the intended center frequency (10 MHz) with 100% bandwidth. The described cMUT was designed to operate at 10 MHz, yielding 107 kPa/V acoustic output pressure per volt, in the collapse-snapback operation.

The collapse-snapback operation utilizes a larger range of membrane deflection profiles (both collapsed and released membrane profiles) and generates higher acoustic output pressures than the conventional and collapsed operations. The collapse-snapback operation is a large signal operation regime which requires the AC voltage amplitude to be larger than the difference between collapse and snapback voltages whereas conventional and collapsed operations can be used with small AC voltages. The collapse-snapback operation of a cMUT with center frequency of 10 MHz was shown to operate around 10 MHz by proper bias and pulse voltages. Since this operation is highly nonlinear, the applied voltages play a crucial role in the collapse-snapback operation characteristics. Experimental results of collapse-snapback operation verify the dynamic FEM results used in the cMUT design process and show the reliable cMUT operation in this regime.

Static and dynamic FEM results predict the generation of around 7 MPa acoustic output pressure around 10 MHz center frequency with 100% fractional bandwidth in the collapse-snapback operation. The voltages used in this operation are close to the voltages used in the conventional operations.

Figure 10:
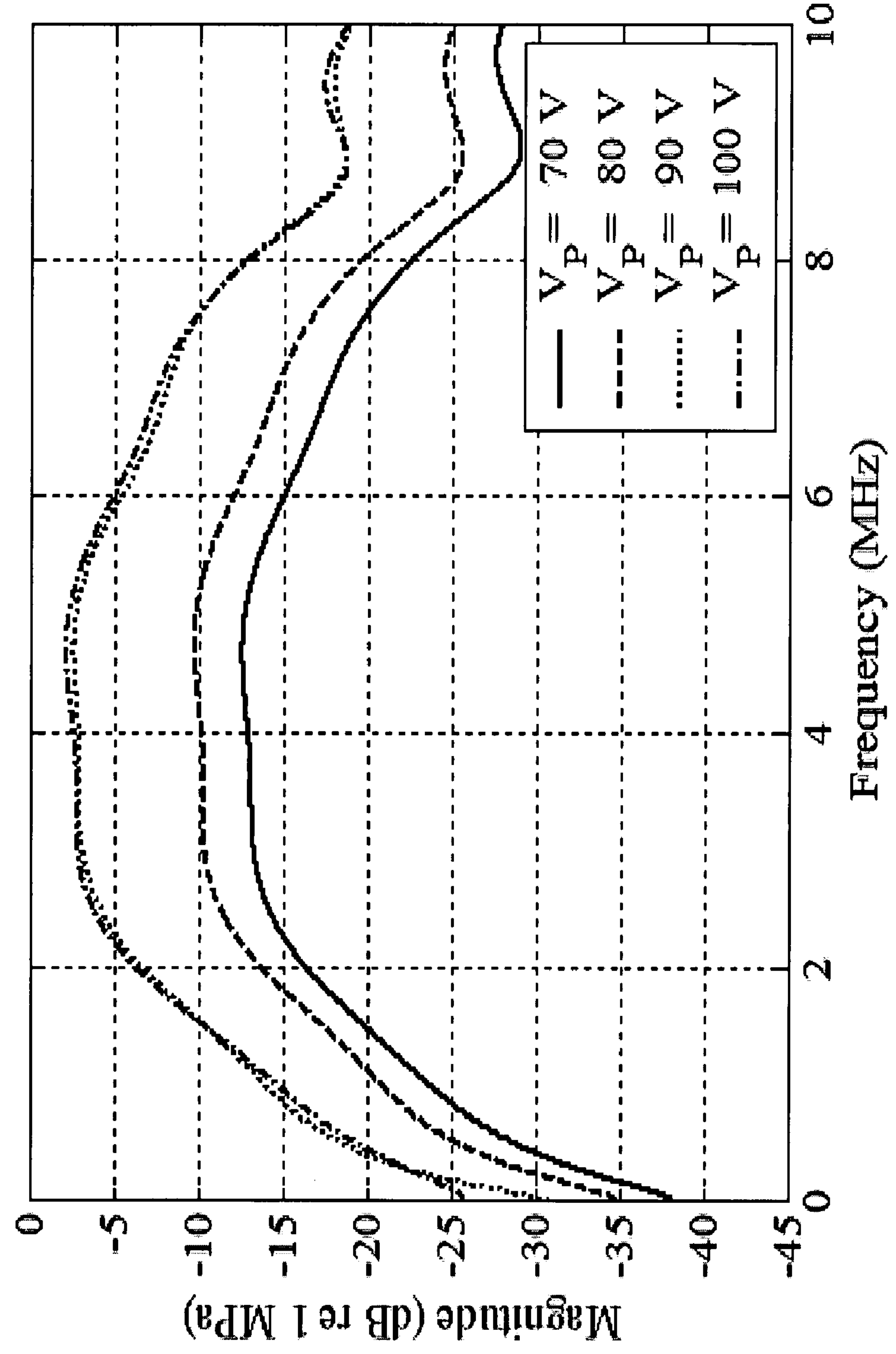
FIG. 10 is a diagram showing experimental results in the form of a graph of Magnitude versus Frequency (MHz).
Figure 11A:
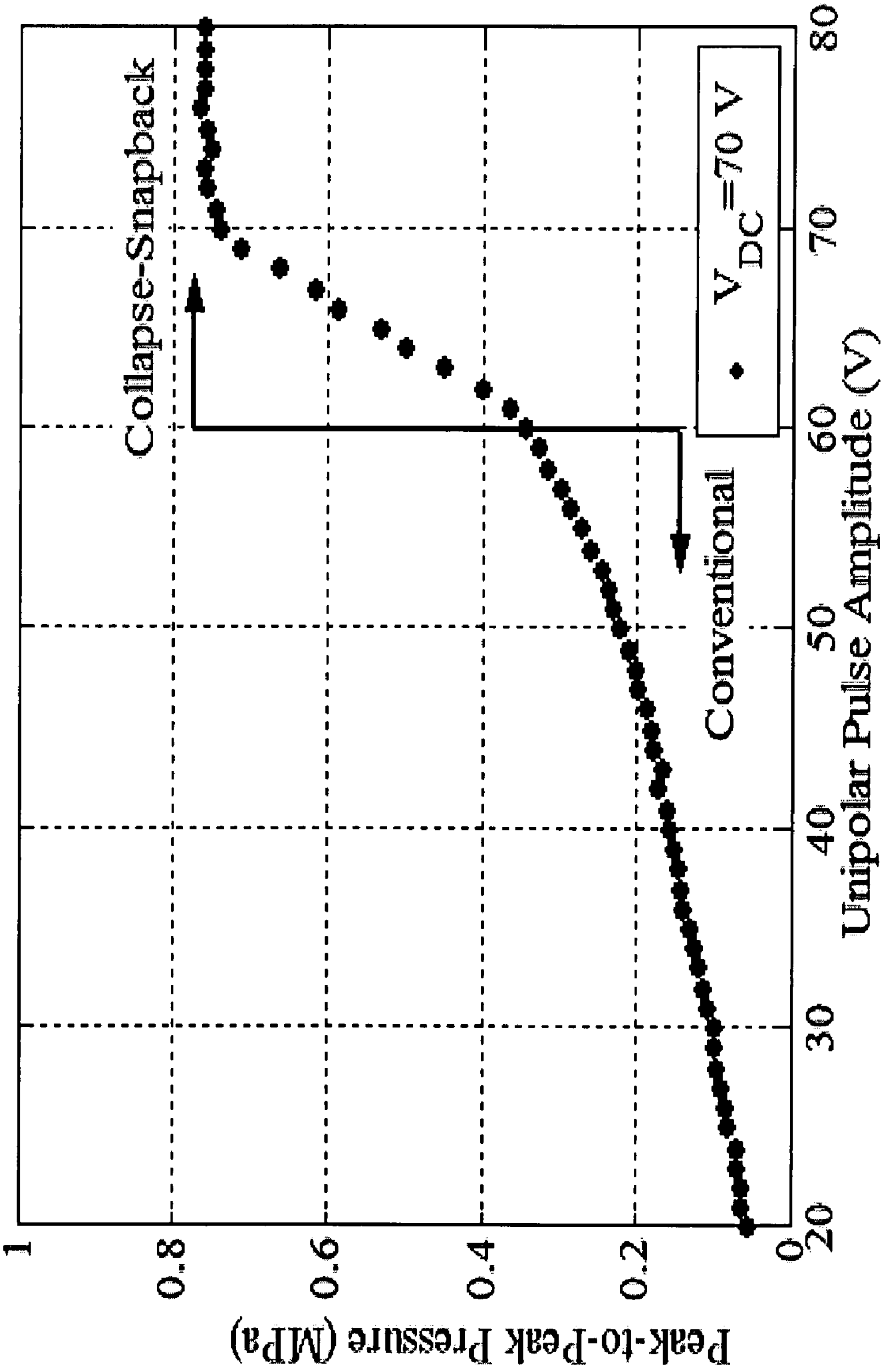
FIG. 11(*a*) is a diagram showing experimental results in the form of a graph of Peak-to-Peak Pressure (MPa) versus Unipolar Pulse Amplitude (V).
Figure 11B:
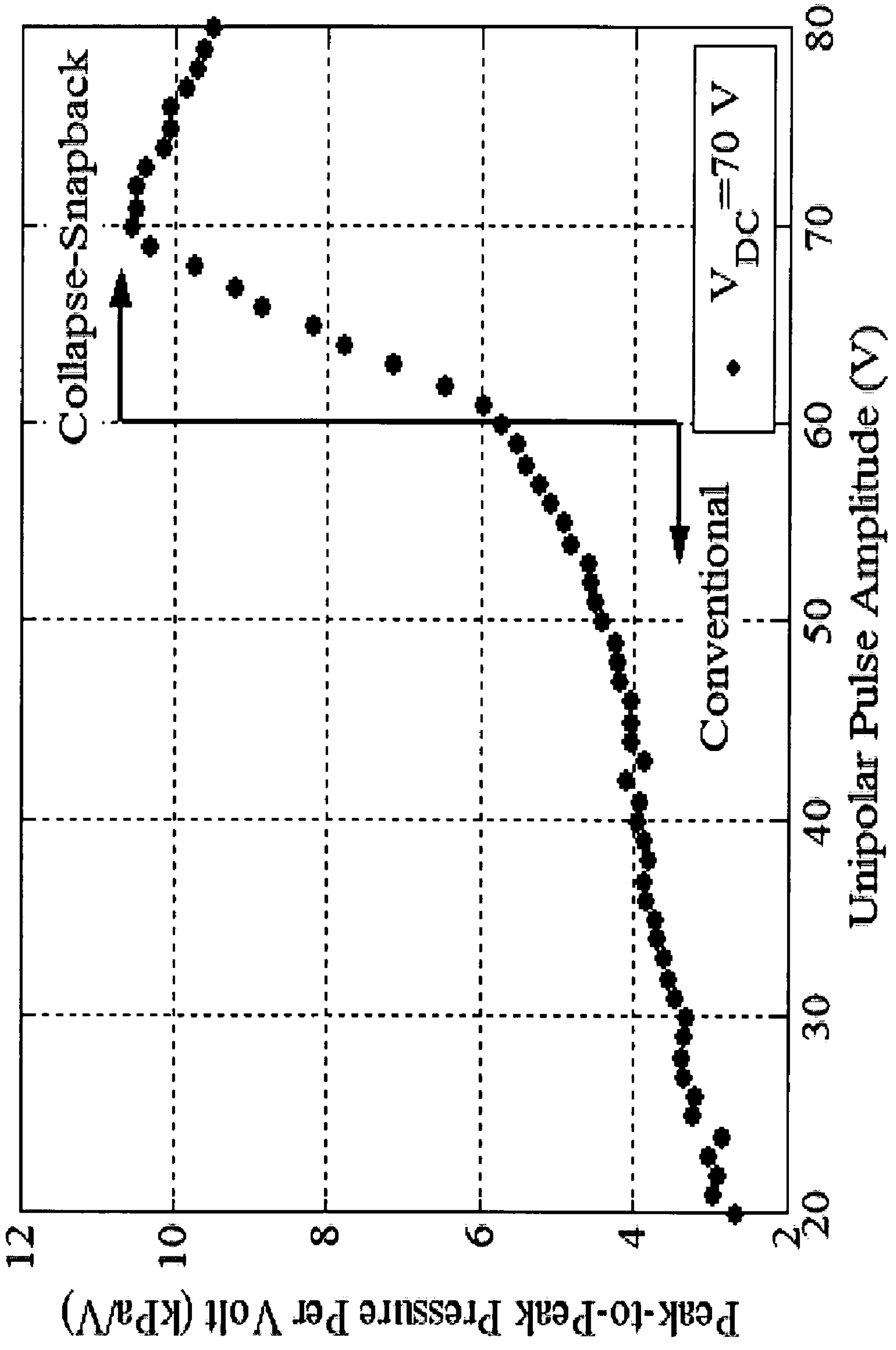
Figure 11C:
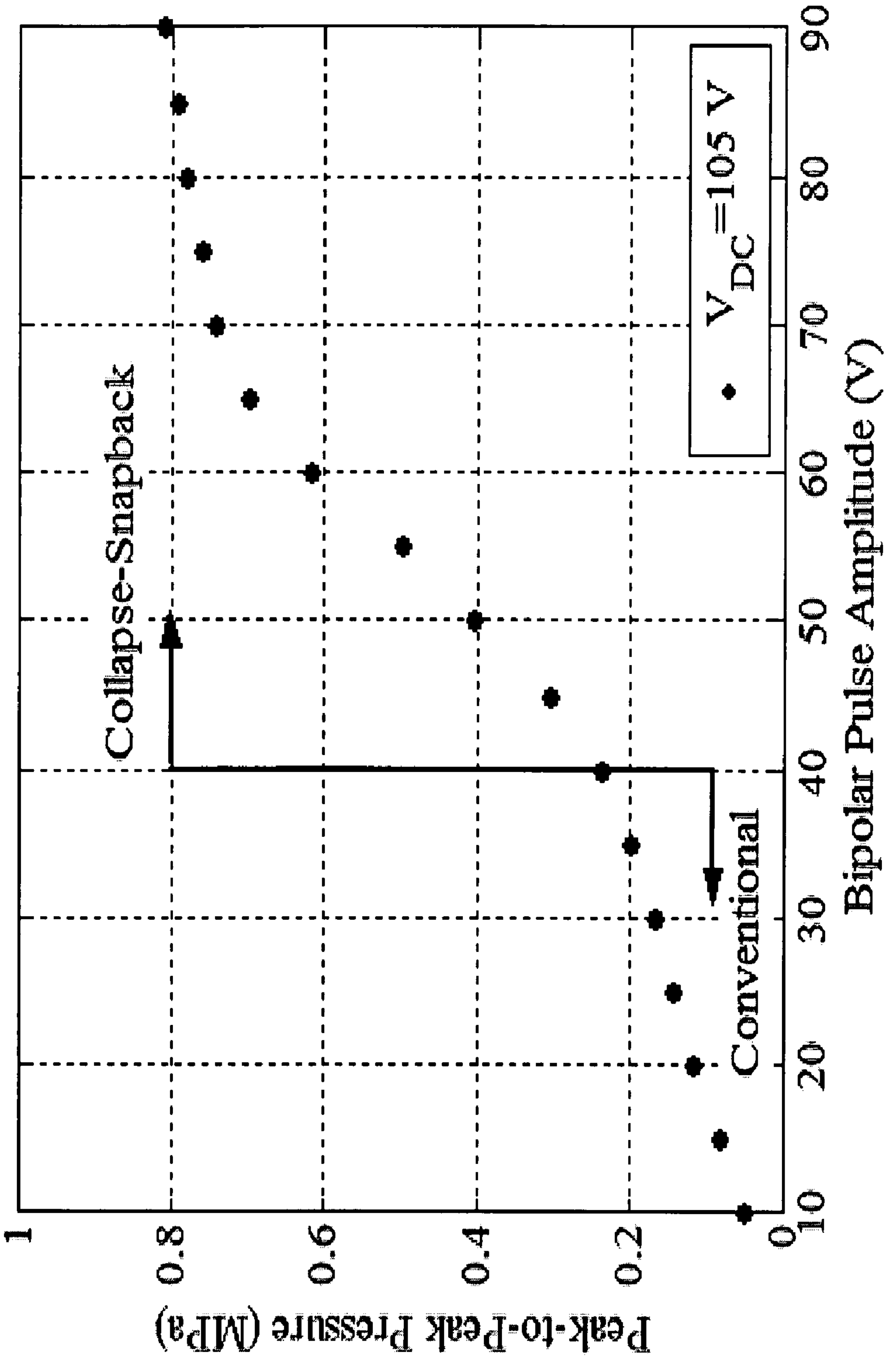
Figure 11D:
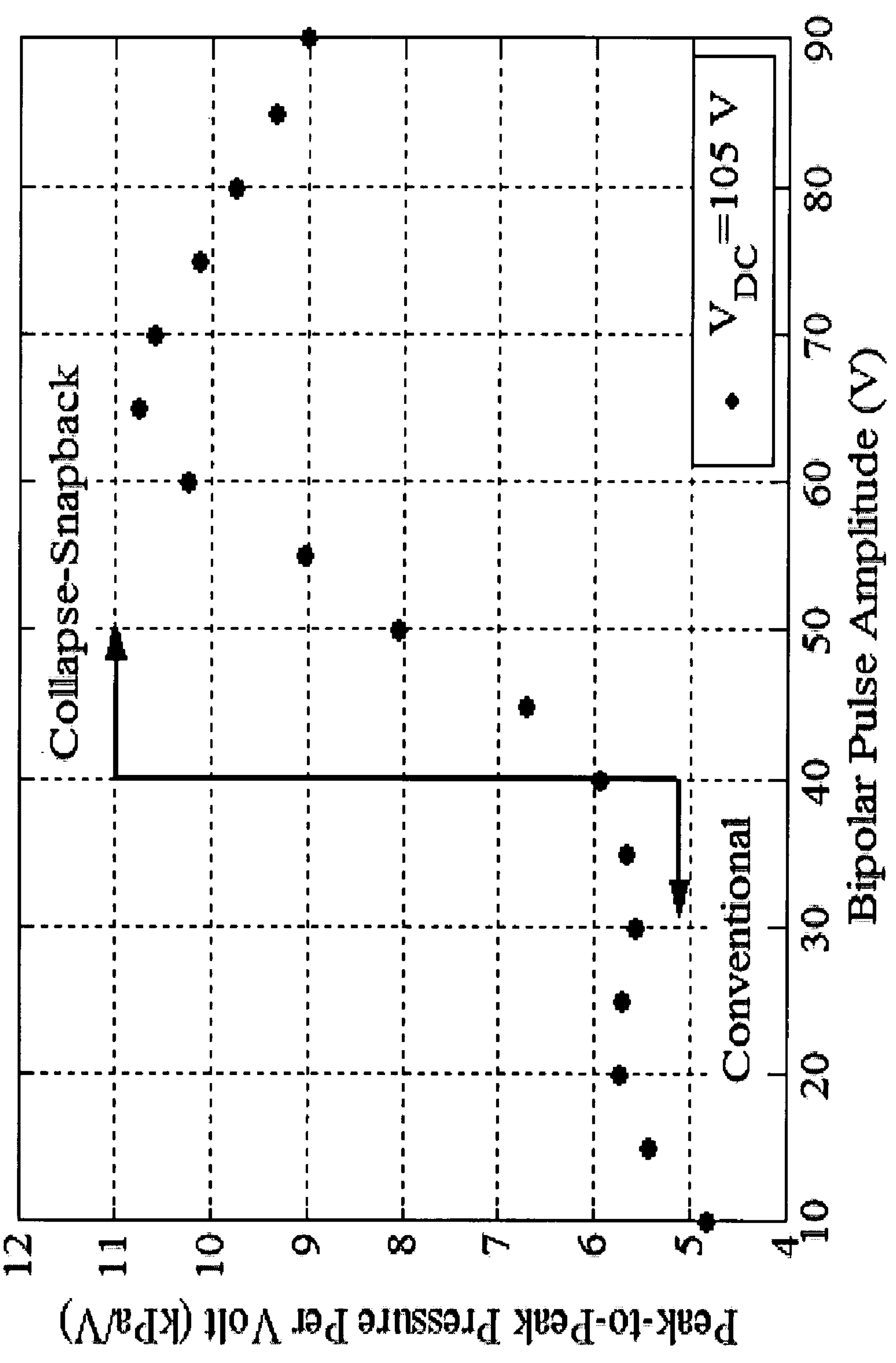
Figure 11E:
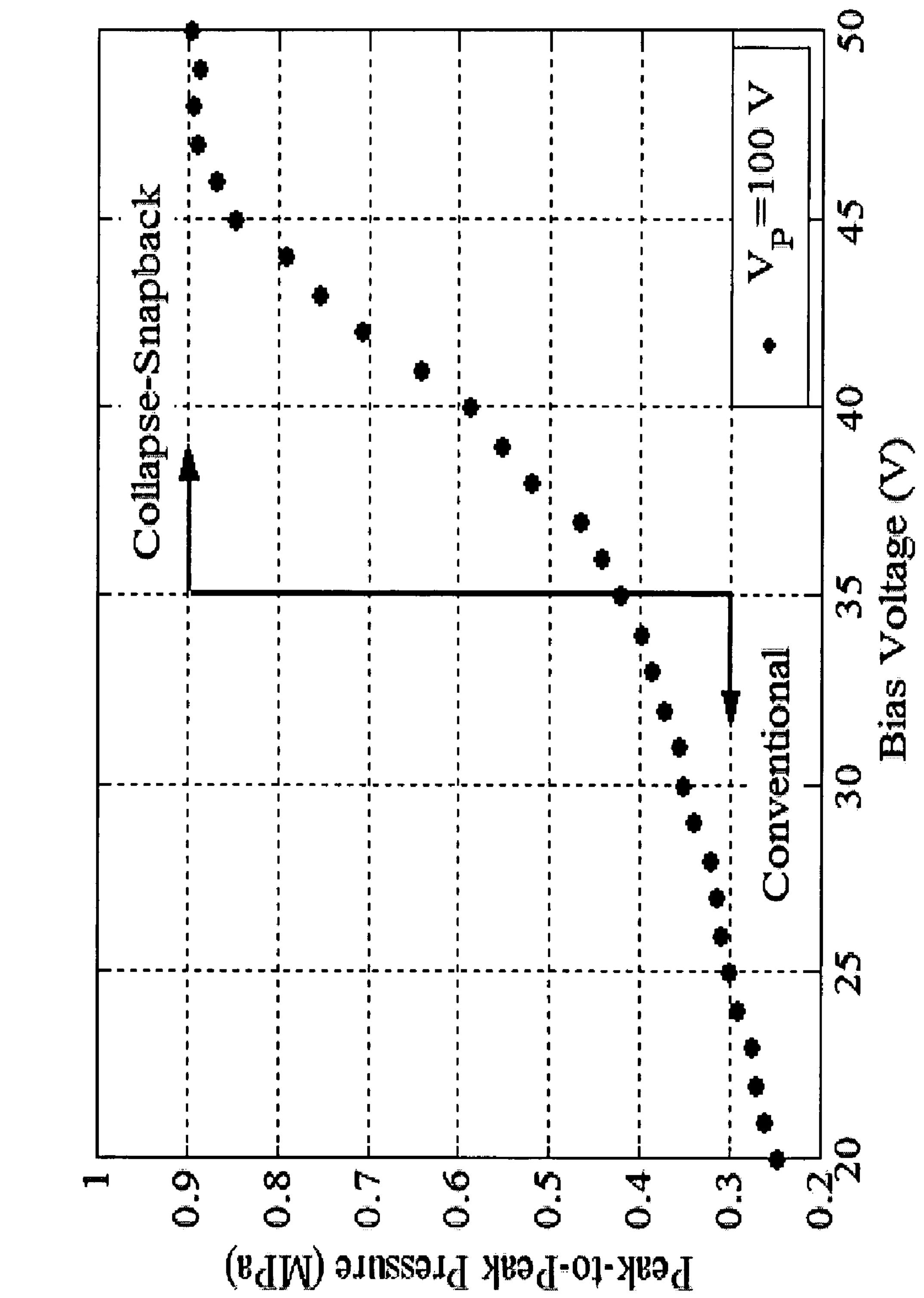
Figure 11F:
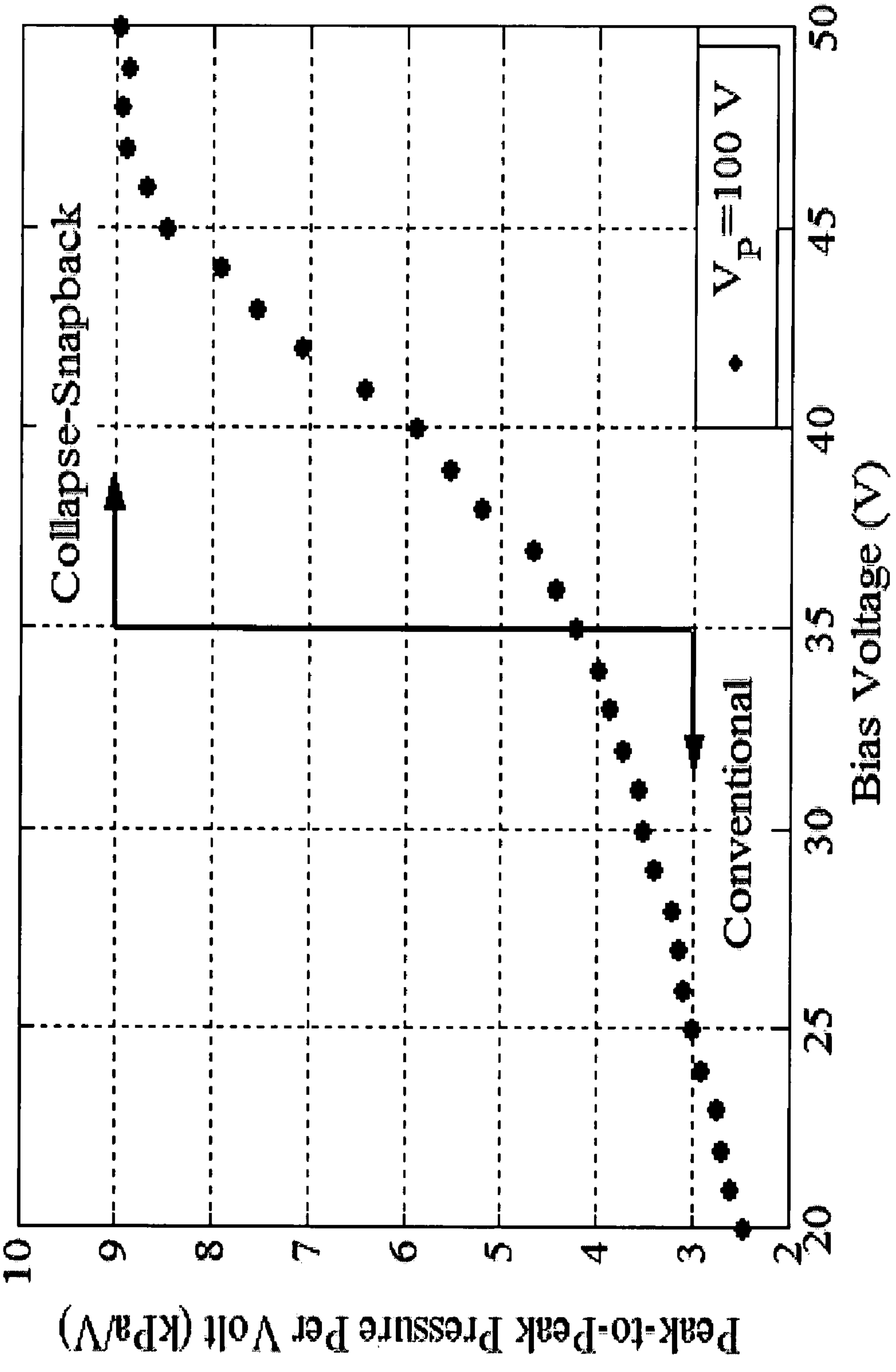

Table II shows physical parameters of a CMUT according to an embodiment of the invention used in experiments for which results are presented in FIGS. 9-11.

TABLE II

| | |
|---|---|
| Length of the transducer, μm | 1180 |
| Width of the transducer, μm | 280 |
| Number of cells per element | 4 × 52 |
| Cell Shape Factor | Hexagon |
| Cell radius, μm | 16 |
| Electrode radius, μm | 8 |
| Electrode thickness, μm | 0.3 |
| Membrane thickness, μm | 1.06 |
| Gap thickness, μm | 0.22 |
| Insulating layer thickness, μm | 0.3 |
| Silicon substrate thickness, μm | 500 |
| Collapse voltage, V | 130 |
| Snapback voltage, V | 110 |

FIGS. 9-11 present experimental data for the CMUT having physical parameters according to Table II.

FIG. 9(*a*) is a diagram showing experimental results in the form of a graph of Average Membrane Pressure (MPa) versus Time (μs).

FIG. 9(*b*) is a diagram showing experimental results in the form of a graph of Average Membrane Pressure (MPa) versus Time (μs).

FIG. 9(*c*) is a diagram showing experimental results in the form of a graph of Average Membrane Pressure (MPa) versus Time (μs).

FIG. 9(*d*) is a diagram showing experimental results in the form of a graph of Average Membrane Pressure (MPa) versus Time (μs).

FIG. 10 is a diagram showing experimental results in the form of a graph of Magnitude versus Frequency (MHz).

FIG. 11(*a*) is a diagram showing experimental results in the form of a graph of Peak-to-Peak Pressure (MPa) versus Unipolar Pulse Amplitude (V).

FIG. 11(*b*) is a diagram showing experimental results in the form of a graph of Peak-to-Peak Pressure Per Volt (kPa/V) versus Unipolar Pulse Amplitude (V).

FIG. 11(*c*) is a diagram showing experimental results in the form of a graph of Peak-to-Peak Pressure (MPa) versus Bipolar Pulse Amplitude (V).

FIG. 11(*d*) is a diagram showing experimental results in the form of a graph of Peak-to-Peak Pressure Per Volt (kPa/V) versus Bipolar Pulse Amplitude (V).

FIG. 11(*e*) is a diagram showing experimental results in the form of a graph of Peak-to-Peak Pressure (MPa) versus Bias Voltage (V).

FIG. 11(*f*) is a diagram showing experimental results in the form of a graph of Peak-to-Peak Pressure (MPa) versus Bias Voltage (V).

What is claimed is:

1. The method of operating a capacitive membrane ultrasonic transducer which comprises the steps of:

determining the voltages which causes the membrane to collapse and snapback;

applying a DC bias voltage which has an amplitude either less than the snapback voltage or greater than the collapse voltage; and thereafter applying a drive voltage greater than the difference between the collapse and snapback voltages to cause the membrane to oscillate between collapse and snapback to generate ultrasonic output pressure waves.

2. The method of claim 1 in which the applied DC bias voltage amplitude is less than the snapback voltage, and the drive voltage causes the membrane to oscillate between snapback and collapse.

3. The method of claim 1 in which the applied DC bias voltage amplitude is greater than the collapse voltage and the drive voltage causes the membrane to oscillate between collapse and snapback.

4. The method of claim 3 in which the applied DC bias voltage amplitude is selected to achieve maximum output for the transducer.

5. The method of claims 1, 2, or 3 in which the drive voltage comprises voltage pulses.

6. The method of claims 1, 2, 3, or 4 in which the voltage is an AC voltage.

7. The method of generating ultrasonic wave energy which comprises: providing a capacitive ultrasonic transducer designed to have selected membrane collapse and snapback voltage; applying a DC bias voltage which has an amplitude either less than the snapback voltage or greater than the collapse voltage; and thereafter applying drive voltages greater than the difference between the selected membrane collapse and snapback voltages which causes the membrane to oscillate between collapse and snapback to generate ultrasonic output pressure waves.

8. The method of claim 7 in which the applied DC bias voltage amplitude is less than the snapback voltage and the drive voltage causes the membrane to oscillate between snapback and collapse.

9. The method of claim 6 in which the applied DC bias voltage amplitude is greater than the collapse voltage and the drive voltage causes the membrane to oscillate between collapse and snapback.

10. The method of claim 9 in which the applied DC bias voltage amplitude is selected to achieve maximum output for the transducer.

11. The method of claim 6 in which the collapse and snapback voltages are equal.

* * * * *

UNITED STATES PATENT AND TRADEMARK OFFICE
CERTIFICATE OF CORRECTION

PATENT NO. : 7,274,623 B2
APPLICATION NO. : 11/094874
DATED : September 25, 2007
INVENTOR(S) : Bayram et al.

It is certified that error appears in the above-identified patent and that said Letters Patent is hereby corrected as shown below:

Col. 1, line 13 insert

--STATEMENT REGARDING FEDERALLY SPONSORED RESEARCH OR DEVELOPMENT

This invention was made with Government support under contracts CA099059 awarded by the National Institutes of Health and N00014-02-1-0007 awarded by the Office of Naval Research. The Government has certain rights in this invention.--

Signed and Sealed this

Twenty-third Day of November, 2010

David J. Kappos
*Director of the United States Patent and Trademark Office*